United States Patent
Bijno et al.

(10) Patent No.: US 9,980,940 B2
(45) Date of Patent: May 29, 2018

(54) COMPOSITION FOR THE TREATMENT OF NEUROPATHIES AND/OR NEUROPATHIC PAIN

(71) Applicant: Kolinpharma S.p.A., Milan (IT)

(72) Inventors: Domenico Bijno, Milan (IT); Carmine Di Vincenzo, Milan (IT); Emanuele Lusenti, Milan (IT); Alberto Martina, Milan (IT); Ritapaola Petrelli, Milan (IT)

(73) Assignee: Kolinpharma S.P.A., Milan (IT)

( * ) Notice: Subject to any disclaimer, the term of this patent is extended or adjusted under 35 U.S.C. 154(b) by 33 days.

(21) Appl. No.: 15/503,080

(22) PCT Filed: Aug. 18, 2015

(86) PCT No.: PCT/IB2015/056266
§ 371 (c)(1),
(2) Date: Feb. 10, 2017

(87) PCT Pub. No.: WO2016/027224
PCT Pub. Date: Feb. 25, 2016

(65) Prior Publication Data
US 2017/0224656 A1    Aug. 10, 2017

(30) Foreign Application Priority Data

Aug. 19, 2014  (IT) .............................. TO2014A0670

(51) Int. Cl.
*A61K 31/385* (2006.01)
*A61K 31/12* (2006.01)
(Continued)

(52) U.S. Cl.
CPC .......... *A61K 31/385* (2013.01); *A61K 9/0053* (2013.01); *A61K 31/12* (2013.01); *A61K 31/221* (2013.01); *A61K 31/355* (2013.01); *A61K 31/375* (2013.01); *A61K 31/51* (2013.01); *A61K 31/525* (2013.01); *A61K 31/675* (2013.01); *A61K 31/714* (2013.01); *A61K 36/9066* (2013.01)

(58) Field of Classification Search
CPC .... A61K 31/12; A61K 31/221; A61K 31/355; A61K 31/375; A61K 31/385; A61K 31/51; A61K 31/525; A61K 31/675; A61K 31/714; A61K 36/9066; A61K 9/0053
See application file for complete search history.

(56) References Cited

U.S. PATENT DOCUMENTS

2005/0074447 A1    4/2005  Papas et al.
2010/0209497 A1*   8/2010  Thornthwaite

OTHER PUBLICATIONS

Meschino, "Supplements That Treat Neuropathies (Part 2)", Dynamic Chiropractic, vol. 32(4), Feb. 15, 2014, pp. 1-6 of 6; downloaded from "www.dynamicchiropractic.com/mpacms/dc/article.php?id=56879".*

(Continued)

*Primary Examiner* — Savitha M Rao
(74) *Attorney, Agent, or Firm* — MacMillan, Sobanski & Todd, LLC

(57) ABSTRACT

A pharmaceutical composition or dietary supplement is described that is effective in the treatment of neuropathies and/or neuropathic pain, comprising, as the active ingredients, a combination of curcumin, N-acetyl-L-carnitine and alpha-lipoic acid.

6 Claims, 15 Drawing Sheets

(51) Int. Cl.
| | |
|---|---|
| A61K 31/221 | (2006.01) |
| A61K 31/355 | (2006.01) |
| A61K 31/675 | (2006.01) |
| A61K 31/714 | (2006.01) |
| A61K 36/9066 | (2006.01) |
| A61K 9/00 | (2006.01) |
| A61K 31/375 | (2006.01) |
| A61K 31/51 | (2006.01) |
| A61K 31/525 | (2006.01) |

(56) References Cited

OTHER PUBLICATIONS

Singh, "From Exotic Spice to Modern Drug?", Cell, vol. 130, 2007, pp. 765-768.*
Abdul, "Involvment of P13/PKG/ERK1/2 signaling pathways in cortical neurons to trigger protection by cotreatment of acetyl-L-carnitine and α-lipoic acid HNE-mediated oxidative stress and neurotoxicity: Implications for Alzheimer's disease", Free Radical Biology & Medicine, 2007, vol. 42, pp. 371-384.
Girl et al., "Curcumin, the active constituent of turmeric, inhibits amyloid peptide-induced cytochemokine gene expression and CCR5- mediated chemotaxis of THP-1 monocytes by modulating early growth response-1 transcription factor", Journal of Neurochemistry, 2004, vol. 91, pp. 1199-1210.
Hsu et al., "Heme Oxygenase-1 Mediates the Anil-Inflammatory Effect of Curcumin Within LPS-Stimulated Human Monocytes", Journal of Cellular Physiology, 2008, vol. 215, pp. 603-612.
Jeon et al., "Curcumin Could Prevent the Development of Chronic Neuropathic Pain in Rats with Peripheral Nerve Injury", Current Therapeutic Research, 2013, vol. 74, pp. 1-4.
Liu et al., "Neuroprotective effect of alpha-lipoic acid on hydrostatic pressure-induced damage of retinal ganglion cells in vitro", Neuroscience Letters, 2012, vol. 526, pp. 24-28.
Mouithys-Mickalad et al., "Effects of COX-2 inhibitors on ROS produced by Chlamydia pneumoniae-primed human promonocytic cells (THP-1)", Biochemical and Biophysical Research Communications, 2004, vol. 325, pp. 1122-1130.
Mosmann, "Rapid Colorimetric Assay for Cellular Growth and Survival: Application to Proliferation and Cytotoxicity Assays", Journal of Immunological Methods, 1983, vol. 65, pp. 55-63.
Papanas et al., "α-Lipoic Acid, Diabetic Neuropathy, and Nathan's Prophecy", Angiology, 2012, vol. 63, pp. 81-83.
Patzko et al., "Curcumin derivatives promote Schwann cell differentiation and improve neuropathy in R98C CMT1B mice", Brain, 2012, vol. 135, pp. 3551-3566.
Tegenge et al., "Curcumin protects axons from degeneration in the setting of local neuroinflammation", Experimental Neurology, 2014, vol. 253, pp. 102-110.
Wang et al., "Amelioration of β-amyloid-induced cognitive dysfunction and hippocampal axon degeneration by curcumin is associated with suppression of CRMP-2 hyperphosphorylation", Neuroscience Letters, 2013, vol. 557, pp. 112-117.
Zanjani et al., "The Attenuation of Pain Behavior and Serum COX-2 Concentration by Curcumin in a Rat Model of Neuropathic Pain", The Korean Journal of Pain, 2014, vol. 27, No. 3, pp. 246-252.
Zhang et al., "α-Lipoic acid attenuates LPS-induced inflammatory responses by activating the phosphoinositide 3-kinase/Akt signaling pathway", PNAS, 2007, vol. 104, No. 10, pp. 4077-4082.
PCT Written Opinion and International Search Report, Application No. PCT/IB2015/056266, dated Nov. 26, 2015.

* cited by examiner

COMPOSITION FOR THE TREATMENT OF NEUROPATHIES AND/OR NEUROPATHIC PAIN

CROSS-REFERENCE TO RELATED APPLICATIONS

This is a national stage application filed under 35 U.S.C. § 371 of international application PCT/IB2015/056266, filed under the authority of the Patent Cooperation Treaty on Aug. 18, 2015, published; which claims the benefit of Patent Application No. TO2014A000670, filed on Aug. 19, 2014. The entire disclosures of all the aforementioned applications are expressly incorporated herein by reference for all purposes.

FIELD OF INVENTION

The invention relates to a composition to be used in the field of the treatment of neuropathies and neuropathic pain.

In particular, the invention relates to a mixture of compounds capable of exerting both a neuroprotective action, mediated by an anti-inflammatory and antioxidant activity, and a neurotrophic and energizing action able to supply nutrients to the fibres and, by increasing the energy metabolism, to restore the damaged membranes and therefore normal nerve conduction.

The invention relates to a formulation for oral administration, without particular contraindications both in relation to the subjects to whom it can be administered and in relation to the amount administered, having an anti-inflammatory, antioxidant and neurotrophic effect and therefore effective in the treatment of neuropathies and neuropathic pain.

BACKGROUND OF INVENTION

Neuropathy is a pathology that affects the peripheral nervous system with the exception of cranial nerve I and II, i.e. the olfactory nerve and the optic nerve respectively. Neuropathy may be localized in one nerve (mononeuropathy) or in several nerves (polyneuropathy).

There are various types of degeneration that affect the nerve fibre:
(i) Wallerian degeneration as a result of interruption of the axon or of the nerve with maintenance of connective tissue: after about 48 hours there is swelling of the axon with myelin destruction and phagocytosis of globular lipid formations; after some days, budding is observed, attributable to the attempt at regeneration with recovery of about 1 mm daily.
(ii) Axonal degeneration as a result of metabolic changes: affects the distal parts of the fibre initially with slow progression in the proximal direction.
(iii) Segmental demyelination through primary damage to the Schwann cells through metabolic changes, inflammatory process, toxic damage: there is a gradual slowing of the impulse, as far as block when demyelination affects a length of fibre greater than 3 internodes, there is axonal distress and an attempt at remyelination on the part of new proliferating cells, but the succession of processes of demyelination and remyelination causes thickening of the fibre by interposition of fibroblasts and collagen, with formation of fibres with "onion bulb" palpable on the skin (Dejerine-Sottas hypertrophic, amyloidotic and chronic inflammatory demyelinating polyneuropathies).

Based on the aetiology, neuropathies may be classified as follows:
  demyelinating inflammatory neuropathies (for example Guillain-Barré syndrome);
  neuropathies due to infective agents (for example HIV, Epstein-Barr, leprosy, sarcoidosis);
  metabolic neuropathies (diabetes, porphyrias, hypothyroidism);
  toxic-nutritional neuropathies (alcohol, hypovitaminosis, drugs, toxic metals);
  paraneoplastic neuropathies;
  paraproteinaemic neuropathies (amyloidotic, gammopathies, cryoglobulinaemias);
  neuropathies in the course of connective-tissue diseases;
  hereditary neuropathies (for example Charcot-Marie-Tooth syndrome).

The peripheral neuropathies are thus a heterogeneous group of diseases of the peripheral nerves. There are multiple causes and, as stated above, they are represented by hereditary and metabolic factors, oxidative stress on the nerve tissue, trauma, infections and inflammations. Most of the peripheral neuropathies are characterized by symptoms such as pain, muscular weakness and sensory loss, which are manifested in general motor disability of the patient.

Neuropathic pain is pathological in that it does not represent a useful and protective function for the organism; in fact, it is characterized by a process of amplification of the nociceptive messages that may be manifested both in the peripheral and in the central nervous system.

In contrast to somatic pain, which arises from particular nerve endings (the pain sensors located in the dermis) and is perceived through tissue damage, neuropathic pain arises directly from a dysfunction of the nerves and does not imply damage in progress.

Neuropathic pain constitutes a common symptom in peripheral neuropathies depending on the length of the nerve, and often represents their initial symptom. Therefore peripheral neuropathies can be defined as a pathological process that mainly affects the myelin fibres of small diameter or the unmyelinated fibres.

Neuropathic pain is associated with numerous types of sensory signs and symptoms that may be manifested alone or together with other specific manifestations in patients with neuropathic pain.

Among the various aetiopathogenic mechanisms hypothesized and demonstrated on the basis of the signs and symptoms of the mechanical peripheral neuropathies, we may mention alteration of the sodium channels (diabetic neuropathies), hyperexcitability of the neurons, sudden changes in spinal connectivity, strong oxidative stress on the nerve tissue. The mediators of inflammatory processes also seem to have a specific role in the onset of degenerative and inflammatory neuropathies.

To summarize, the causes of painful symptomatology of the upper and lower limbs are numerous and of varied origin, and may be of orthopaedic interest (myalgias, compressive or traumatic neuropathies). In fact, a high percentage of these painful syndromes of the limbs are to be attributed to irritative or compressive radiculopathies, with cervical relevance in the case of the upper limbs, and lumbosacral with respect to the lower limbs, the commonest cause of which is a herniated disc.

BRIEF SUMMARY OF INVENTION

The composition according to the present invention, effective in the treatment of neuropathies and neuropathic pain, is characterized in that it comprises, as the active ingredients, a combination of curcumin, N-acetyl-L-carnitine and alpha-lipoic acid.

Further characteristics of the composition of the invention and of its use are defined in the appended claims that form an integral part of the present description.

Curcumin, IUPAC name (1E,6E)-1,7-bis(4-hydroxy-3-methoxyphenyl)-hepta-1,6-diene-3,5-dione, is a compound belonging to the class of polyphenolic compounds. It is obtained by solvent extraction from the dried and powdered rhizome of the *Curcuma longa* plant.

*Curcuma longa* is a plant originating from South-East Asia and is used traditionally as a spice. This plant is known from ancient times for its high antioxidant properties and is used traditionally for the treatment of inflammation, gastro-intestinal disorders, hepatic disorders and other disorders. Its capacity to withstand the action of free radicals is far greater than that of the other known natural antioxidants. *Curcuma* is in fact rich in active ingredients, in particular curcuminoids and among these more particularly curcumin. Owing to its antioxidant and anti-inflammatory activity, *Curcuma longa* is regarded as a cellular bioprotector, able to contribute actively to restoration of the basal conditions of the compromised neuronal environment.

In contrast to other antioxidants, the curcuminoids are capable both of preventing the formation of free radicals and of potentiating the activity of alpha-lipoic acid, neutralizing the radicals already present in the tissues.

Regarding the anti-inflammatory activity, there are numerous studies that confirm the action of *curcuma* at various levels, allowing it to be regarded as a very potent inhibitor of the inflammatory cascade: at genic level, it inhibits expression of cycloxygenase-2, inhibits the activity of lipoxygenase-5 and production of prostaglandins by cycloxygenases 1 and 2. It also inhibits activation of proinflammatory cytokines (TNF-α; IL-1β), the adhesion molecules, growth factor receptors and vascular endothelial growth factor (VEGF), activities correlated with tumour onset.

In the formulations according to the invention, *Curcuma longa* extract constitutes the preferred source of curcumin. More preferably, a *Curcuma longa* extract that has a curcumin titre of 95% is used. *Curcuma longa* extracts also comprise some curcumin derivatives, generally known as curcuminoids, among which we may mention in particular demethoxycurcumin and bisdemethoxycurcumin.

Alpha-lipoic acid (ALA) is a very small vitamin occurring in nature in two forms, the oxidized form (cyclic disulphide) and the reduced form (dihydrolipoic acid, with two sulphydryl groups in position 6 and 8). The two forms are quickly interconvertible and, at the level of damaged tissue, behave as neuroprotector and neurotrophic and, at the systemic level, as a euglycaemic agent (a fundamental activity as most diabetic patients are affected by neuropathies).

The neuroprotective action results from the known antioxidant activity, which is able to reduce oxidative stress at the level of damaged nerve tissue. The presence of free radicals causes deterioration of the cell membranes and in particular of the Schwann cells, reducing the functionality of the nerve and the transmission performance, as well as activating non-physiologically the transduction pathways linked to NF-kB, which stimulates the immune response (inducing inflammation), regulates cellular proliferation and the apoptotic cascade, but is also involved in the onset of cancer and autoimmune diseases. Alpha-lipoic acid is particularly effective in neutralizing free radicals: in fact it acts as a scavenger, but is also able to restore other potent antioxidants at the cellular level, such as vitamin E, vitamin C, coenzyme Q and reduced glutathione.

Alpha-lipoic acid is moreover able to inhibit phagocytic chemotaxis at the level of neuronal damage and this represents confirmation that the composition according to the invention, comprising alpha-lipoic acid, is able to bring about reduction of inflammation and inhibition of damage. In fact, in the case of degeneration of nerve fibres, macrophages rush to the affected site and phagocytize the surrounding myelin, amplifying the damage and further reducing the conductive capacity of the neurons involved, as well as amplifying the response on the part of the inflammatory cascade.

Alpha-lipoic acid also exerts a neurotrophic action at two levels: increasing energy metabolism and inducing production of NGF (nerve growth factor). The energy metabolism is sustained by the presence of alpha-lipoic acid since, already physiologically, it is a cofactor of two key enzyme complexes involved in the Krebs cycle. The first complex is pyruvate dehydrogenase, which catalyses oxidative decarboxylation of pyruvate to acetyl-CoA, while the second is α-ketoglutarate dehydrogenase, which catalyses conversion of α-ketoglutarate to succinyl-CoA, also in this case by oxidative decarboxylation. The two enzyme complexes are similar and the decarboxylation reactions take place with production of a high-energy thioester bond with coenzyme A, which is possible owing to the availability of the sulphydryl groups of ALA. The Krebs cycle is a metabolic cycle of fundamental importance in all cells; it permits the formation of chemical energy (ATP) by degradation of carbohydrates, fats and proteins, but also supplies many precursors for the production of amino acids and other fundamental molecules in the cell. At nerve tissue level it is fundamental to supply energy, both for maintaining the basal functions of the cells, and for restoring membranes damaged by inflammation and by oxidative stress, and for the production of neurotransmitters and vesicles that are fundamental for cell-cell communication, or for nerve conduction, which is degraded in the case of neuropathies.

In addition to potentiation of energy metabolism, alpha-lipoic acid is able to improve the production of NGF. NGF is a signal protein involved in development and maintenance of the nervous system. This factor promotes and directs axonal growth and, by means of cell signalling mechanisms, is an indispensable product during regeneration, as a growth factor.

It is known that most individuals with diabetes are liable to complications connected with neuropathic pain. This represents another reason why the composition according to the invention includes alpha-lipoic acid, which has euglycaemic activity, i.e. is able to intervene in saccharide metabolism, resensitizing the insulin receptors and restoring the physiological activity of insulin itself, assisting drug treatment.

The third component of the composition according to the invention is N-acetyl-L-carnitine, i.e. the acetyl ester of L-carnitine, a compound present physiologically in all mammals. The compound is metabolized in the blood to carnitine, thanks to plasma esterases. The main function of carnitine is transport of long-chain fatty acids from the cytoplasm to the mitochondrial matrix, as a result of their activation to acyl-CoA. Once in the matrix, the fatty acids are utilized and oxidized. The function of carnitine is connected with the intracellular regulation of a correct ratio between acyl-CoA and acyl-carnitine, by transferring short-chain acyl groups from inside the mitochondrion to the cytoplasm. The availability of L-carnitine and its esters such as N-acetyl-carnitine prevents accumulation of fatty acids and acyl-CoA, in the cytoplasm and in the mitochondrion respectively, and permits establishment of acetyl-CoA at the mitochondrial site for the production of energy by the beta oxidation cycle. Excess of acetyl-CoA would cause an increase in the number of carbohydrates that can be used for energy purposes to the detriment of the fatty acids. It is therefore interesting to note that in diabetic subjects the ingestion of N-acetyl-carnitine can improve glucose metabolism.

The presence of N-acetyl-carnitine in the composition according to the invention is particularly advantageous because this substance acts on several fronts in synergy with alpha-lipoic acid. N-acetyl-carnitine has neurotrophic activity, being able to increase the level of production of NGF and induce an increase in the sensitivity of neuronal receptors to the growth factor, amplifying its responses. This aspect is important for induction of the production of the myelin sheath necessary for maintaining the health and functionality of the nerve, as well as for restoring its physiological conditions in case of damage.

Together with alpha-lipoic acid, with which it exerts a synergistic effect, N-acetyl-carnitine is able to potentiate neuronal protection, regulating at gene level the pathways involved in cellular growth (a fundamental aspect for induction of sprouting and for synaptogenesis), in the activation of anti-apoptotic proteins (to counteract the apoptotic cascade induced by NF-kB in the case of strong oxidative stress and/or damage at nerve fibre level) and antioxidants (for neutralizing the environment surrounding the damaged neurons and/or for preventing oxidative damage).

The combination of the aforementioned active ingredients in the composition according to the invention is particularly advantageous since they develop a synergistic effect, both with regard to neuroprotective action and with regard to neurotrophic action.

According to a preferred aspect of the present invention, the compositions in question will be able to contain additional components, with therapeutic action, or supplementary action, or otherwise useful for the proposed purposes of the invention. Examples of said additional components are vitamin C, vitamin E, vitamin B1, vitamin B2, vitamin B6 and vitamin B12.

Vitamin B1, or thiamine, is a water-soluble vitamin which, once it reaches the tissues, is phosphorylated to thiamine diphosphate (or pyrophosphate), its active form. Thiamine pyrophosphate (PP) is the coenzyme of the decarboxylases of keto acids and transketolases. In fact it performs an important role in the oxidative decarboxylation of pyruvate and of α-ketoglutarate (synergy with ALA) in the Krebs cycle and in the transketolase reaction in the pentose phosphate cycle.

Vitamin B2, or riboflavin, is a heterocyclic compound obtained from a molecule of flavin that is bound to a chain formed from ribitol. Riboflavin, once metabolized, is transformed to flavin mononucleotide (FMN) and flavin adenine dinucleotide (FAD), two coenzyme forms essential for the flavin enzymes in which they function as prosthetic groups. They take part in various redox reactions in the metabolism of carbohydrates, proteins and lipids, including oxidative decarboxylation of pyruvate, oxidation of fatty acids and amino acids, and transport of electrons during oxidative phosphorylation.

Vitamin B6, in the three forms pyridoxine, pyridoxal and pyridoxamine, participates in the mechanisms of neuroprotection, as well as promoting conversion of tryptophan to serotonin, providing reduction of painful symptoms.

Vitamin B12, or cobalamin, participates in repair processes of the myelin sheath in that it participates in the synthesis of phospholipids, catecholamines and phosphatidylcholine (membrane structural elements).

Vitamin E, or tocopherol, is a fat-soluble vitamin regarded as the antioxidant vitamin par excellence. In the composition according to the invention its purpose is to increase lipid production at neuronal membrane level, the first targets of free radicals.

Vitamin C, or ascorbic acid, is also fundamental for its known antioxidant properties. This function is exerted when vitamin C undergoes autoxidation and then regenerates oxidized substances such as iron or copper, returning them to their original form. During this process, the harmful oxidizing agent is removed. It is able to block reactive oxygen species (ROS, such as superoxide, peroxyl and hydroperoxyl radicals), but also nitrogen (RNS, such as the nitroxide, peroxynitrite radicals and nitrogen dioxide) that may form at the site of inflammation. Vitamin C is a fundamental element for correct functioning of the brain and nervous system, and in fact in conditions of stress it is consumed more quickly.

The compositions of the invention can be formulated in any form suitable for oral administration, for example as hard or soft gelatin capsules, tablets, effervescent or chewable tablets, granules or powders in sachets, solid forms with controlled release, chewing gums and similar.

The compositions of the present invention can be formulated in a way that is suitable for administration by the oral route and will be prepared by conventional methods that are well known in pharmaceutical technology, such as those described in "Remington's Pharmaceutical Handbook", Mack Publishing Co., N.Y., USA, using excipients, diluents, fillers, and anti-caking agents that are acceptable for their end use.

BRIEF DESCRIPTION OF THE DRAWINGS

The experimental section that follows describes the studies that have been carried out relating to the biological effects of the composition of the invention. In the description of the studies conducted, reference is made to the appended figures, in which.

DETAILED DESCRIPTION OF THE INVENTION

Figure 1:
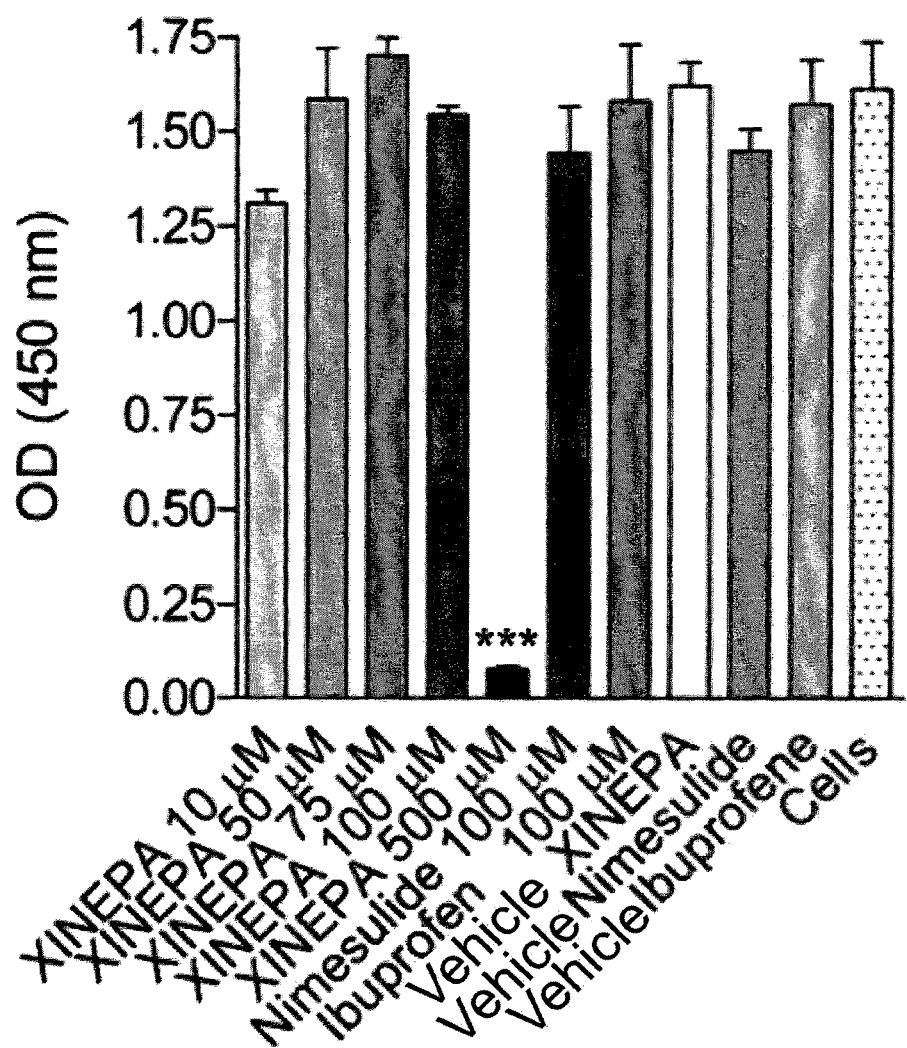
FIG. 1 is a representation of the results obtained with the MTT assay on THP-1 cells incubated with Xinepa. The absorbance at 450 nm was measured in the various wells incubated for 16 hours with the stated compounds at the stated concentrations. Each bar represents the mean value of at least 4 different wells. (***=$p<0.001$)

A particularly preferred formulation of the composition of the invention, used in the experimental studies, is presented hereunder.

Formulation Example—1.08 g Tablet

TABLE 1

| | |
|---|---|
| N-acetyl-carnitine | 400 mg |
| Alpha-lipoic acid | 300 mg |
| *Curcuma longa* dry extract | 150 mg |
| of which *curcuma* | 142.95 mg |
| Vitamin C | 125 mg |
| Vitamin E | 9 mg |
| Vitamin B1 (thiamine) | 6.25 mg |
| Vitamin B2 (riboflavin) | 6.25 mg |
| Vitamin B6 (pyridoxine) | 2.38 mg |
| Vitamin B12 (cyanocobalamin) | 6.25 mg |

The recommended dose is one or two tablets daily.

Example 1. Evaluation of Anti-Inflammatory Activity and Quantification of Oxidative Stress Rationale The composition of the invention has, as pathological target, neuropathic pain from trauma or from an inflammatory effect. Neuropathic pain is a chronic condition caused by lesions or dysfunctions of the somatosensory nervous system. Damage to a peripheral nerve may cause amplification of the response, as a result of painful stimuli applied peripherally, at the level of the first synapse of the nociceptive pathway, causing neuronal hyperactivity at spinal cord level. The non-neuronal cells have a key role in the molecular mechanisms of neuropathic pain. In particular, as a result of damage of a peripheral nerve, alteration of the "blood-spinal cord barrier" (BSCB) may be observed, with consequent infiltration of macrophages and T-lymphocytes. These cells of the peripheral immune system, together with astrocytes and microglial cells, secrete pro-inflammatory cytokines and chemokines causing sensitization of the neurons of the first synapse of the nociceptive pathway. Inhibition of the pro-inflammatory cytokines and induction of expression of anti-inflammatory cytokines may bring about attenuation of nociception.

Purpose of the Study

The present study analysed two of the aspects involved in the onset and persistence of neuropathic pain, inflammation and oxidative stress. Therefore two different cellular assays were developed:

Assay 1: Evaluation of anti-inflammatory activity in a cell line of human monocytes (THP-1).

Assay 2: Quantification of oxidative stress in a cell line of human monocytes (THP-1).

Prior to these two assays, Assay 0 was carried out to define the incubation times and the product concentrations to be used without encountering phenomena of cellular toxicity.

Materials and Methods

Xinepa

In the experimental tests presented below, the formulation as tablets of the Formulation Example given above, designated Xinepa, was used.

Xinepa proved to be insoluble in water, 100% ethanol, methanol, ethyl acetate, DMSO, as some of its components are soluble in water but not in alcohols (such as vitamin B2), or soluble in alcohols or organic solvents but not in water (such as lipoic acid and *curcuma*). For this reason the individual ingredients of Xinepa were solubilized, each in the appropriate solvent, and then mixed again to reproduce the product Xinepa.

The concentration of lipoic acid (LA) 500 μM was taken as the reference, its anti-inflammatory effect in THP-1 cells being known (Zhang W-J et al., PNAS, 2007, Vol. 104, pages 4077-4082). Based on the LA concentration, the other components were added to form the final compound, maintaining the same relative amounts present in Xinepa, as illustrated in the Formulation Example. With these preparation conditions, the final solution with which the cells were incubated during the tests was transparent.

The positive controls with which we compared the effects determined with Xinepa in the various tests carried out are: dexibuprofen and nimesulide for anti-inflammatory effect (assay 1), Vitamin E and Vitamin B6 for antioxidant effect (assay 2).

Cells

Human THP-1 cells derived from acute monocytic leukaemia (ATCC, cat. No. TIB-202) were cultured in RPMI-1640 medium (Life Technologies, cat. No. 21870-076) with addition of Na pyruvate 1 mM, HEPES 10 mM, L-glutamine 2 mM, 2-mercaptoethanol 0.05 mM, and fetal bovine serum at final concentration of 10%. The cells were kept in an incubator at 37° C. and 5% $CO_2$ and sown every 3-4 days at a density of about $5\times10^5$ cells/ml. For all the tests undertaken, the cells were sown in the evening in 96-well plates and incubated with various concentrations of Xinepa, of its vehicle, and of the positive control(s) in complete medium.

After incubation for about 16 hours, the cells were differentiated in serum-free medium for 2 hours in the presence or absence of lipopolysaccharide (LPS) (1 μg/ml).

MTT Assay (Assay 0)

To verify that incubation with Xinepa at the concentrations and for the times selected is not toxic for the cells, one or more MTT assays (Assay 0) were carried out. This colorimetric assay is based on the transformation of tetrazolium salt MTT (yellow) to formazan (violet), by the reductase succinate-tetrazolium system, which belongs to the respiratory chain of the mitochondria and is only active in metabolically active cells. Briefly, the cells grown in a 96-well plate were incubated with the solution of MTT for 4 hours. In this period, an insoluble dye forms, which after it has been solubilized by adding the solubilizing solution (10% SDS in 10 mM HCl) to the samples and after incubation overnight in the incubator, can be quantified by reading the absorbance of the samples at 595 nm (using 750 nm as the reference wavelength). The absorbance measured correlates directly with the number of live cells.

ELISA Assay (Assay 1a)

The anti-inflammatory effect of Xinepa was studied using the ELISA assay (Enzyme-Linked Immunosorbent Assay, Biolegend, Inc.), quantifying the production of proinflammatory cytokines in the culture medium following treatment with Xinepa and with the various controls.

In "sandwich" ELISA, a 96-well plate is coated with a monoclonal antibody specific for a particular cytokine. The standards and the samples are added to the wells and the cytokine of interest binds the capture antibody immobilized on the bottom of the well. Next a biotinylated anti-cytokine antibody is added to the wells so that the antibody-antigen-antibody "sandwich" is formed. Horseradish peroxidase conjugated to streptavidin is then added, followed by a solution of tetramethylbenzidine (TMB) which, on reacting with the peroxide, produces a compound coloured blue, whose intensity is proportional to the amount of cytokine present. Addition of a solution of sulphuric acid changes the colour of the solution from blue to yellow, blocking the development of the colour and allowing accurate reading of the absorbance of the samples at 450 nm.

The cells incubated with the various treatments overnight were then differentiated for 2 hours in serum-free medium and concomitantly stimulated with LPS (lipopolysaccharide, one of the components of the outer membrane of Gram-negative bacteria). At the end of the treatment the supernatant was collected and stored at −80° C. until it was used for the assay.

Nuclear Translocation of NF-kB (Assay 1b)

After incubation overnight with the various treatments, the THP-1 cells were sown on slides functionalized with poly-L-lysine 0.01% in the presence of LPS 1 μg/ml for 2 hours. After the 2 hours the cells were fixed with paraformaldehyde 4% in PBS (15 min), permeabilized with a solution of Triton X-100 0.2% in PBS (10 min) and the nonspecific binding sites with the primary antibody were blocked with 1% BSA solution in PBS (30 min). In the same blocking solution, incubation was carried out with the anti-NF-kB p65 antibody (Biolegend Inc.) diluted 1:200 (2 hours at room temperature), followed by incubation with the secondary antibody conjugated to the Atto488 fluorophore, diluted 1:200 in the blocking solution. The DNA was labelled with Hoechst33342 to identify the nuclei and the slides were mounted with Prolong Gold (Life Technologies).

The samples thus prepared were acquired in the confocal microscope (TCS SP5 AOBS, Leica Microsystems) and the images were analysed with the ImageJ v1.47h software (http://imagej.nih.gov/ij) for quantifying the nuclear translocation of NF-kB (Noursadeghi M. et al., Journal of Immunological Method, 2008, Vol. 329, pages 194-200). For each sample, at least 10 images were acquired, referred to the nuclear signal (Hoechst33342) and to the signal of NF-kB (Atto488) with 20× objective (HC PL APO CS, NA 0.5, Leica Microsystems). For each field, the binary images of the signals of NF-kB and of Hoechst33342 were created, using an automatic threshold. The mask relating to the signal of Hoechst33342 was used for defining the nuclear ROI (regions of interest). The nuclear masks were then removed from the binary image of NF-kB to define the cytoplasmic ROI. These masks were then applied to the original signals of NF-kB to calculate the fluorescence intensity in the nucleus and in the cytoplasm from the histograms of the intensities created with ImageJ. The average ratio of fluorescence intensity between nucleus and cytoplasm was then calculated for each sample.

Evaluation of the Intracellular Levels of ROS (Assay 2)

The oxidative stress in THP-1 cells pre-incubated with Xinepa or with the various controls and stimulated with 100 mM $H_2O_2$ for 2 hours during the period of differentiation in serum-free medium was quantified by means of a fluorogenic probe, CellROX® Deep Red Reagent (Life Technologies) capable of measuring the reactive oxygen species (ROS) in living cells. The operating principle of the probe is based on the fact that it is not fluorescent in the reduced state, whereas following oxidation it develops a fluorescent signal with excitation peak at 640 nm and emission peak at 665 nm. Briefly, at the end of the period of stimulation with $H_2O_2$, the cells were incubated with CellROX® Deep Red Reagent at a final concentration of 5 µM in the medium at 37° C. for 30 min. The nuclei were labelled with Hoechst33342 and the fluorescences of both channels (CellROX® Deep Red and DAPI) were read on the GloMax plate fluorometer (Promega Italy). The fluorescence signals relating to the ROS were normalized for the signal of Hoechst33342 to cancel the variability in the fluorescence signal read due to the number of cells present in each well.

The same plates were then also acquired in the confocal microscope for the purpose of obtaining representative images relating to quantifications of the various treatments.

Statistical Analysis

The quantitative data relating to the various assays were expressed as mean±standard error. The one-way ANOVA statistical test (comparison between more than two groups) or t-test (comparison between two groups) with non-coupled data was used for identifying statistically significant differences between the various samples.

Results

Identification of Doses and Treatment Times (Assay 0)

The THP-1 cells were incubated overnight with successive dilutions of Xinepa, starting from the composition having the concentration of lipoic acid 500 µM as reference. To exclude a possible toxic effect attributable to the incubation protocol selected, cellular vitality was quantified by the MTT assay. The data obtained on two different experiment days are summarized in FIG. 1.

Since the highest concentration of Xinepa caused high cellular mortality, the next assays were carried out with Xinepa 50, 75 and 100 µM. At these concentrations of the compound, the measured absorbance was not statistically different from the control (cells incubated with the vehicle of Xinepa referred to the highest concentration). Similarly, incubation with the positive controls nimesulide and ibuprofen at a concentration of 100 µM (Mouithys-Mickalad A. et al., BBRC, 2004, Vol. 325, pages 1122-30) did not identify any effect of toxicity on the cells.

Anti-Inflammatory Activity in a Line of Human Monocytes (Assay 1)

The anti-inflammatory activity of Xinepa was studied with two different experimental approaches: on the one hand, possible inhibition of the production of pro-inflammatory cytokines was quantified by ELISA assay (Assay 1a), and on the other hand possible inhibition of the nuclear translocation of NFkB was quantified by immunolabelling in fluorescence and image acquisition with the confocal microscope (Assay 1b).

ELISA Assay, Assay 1a

Figure 2:
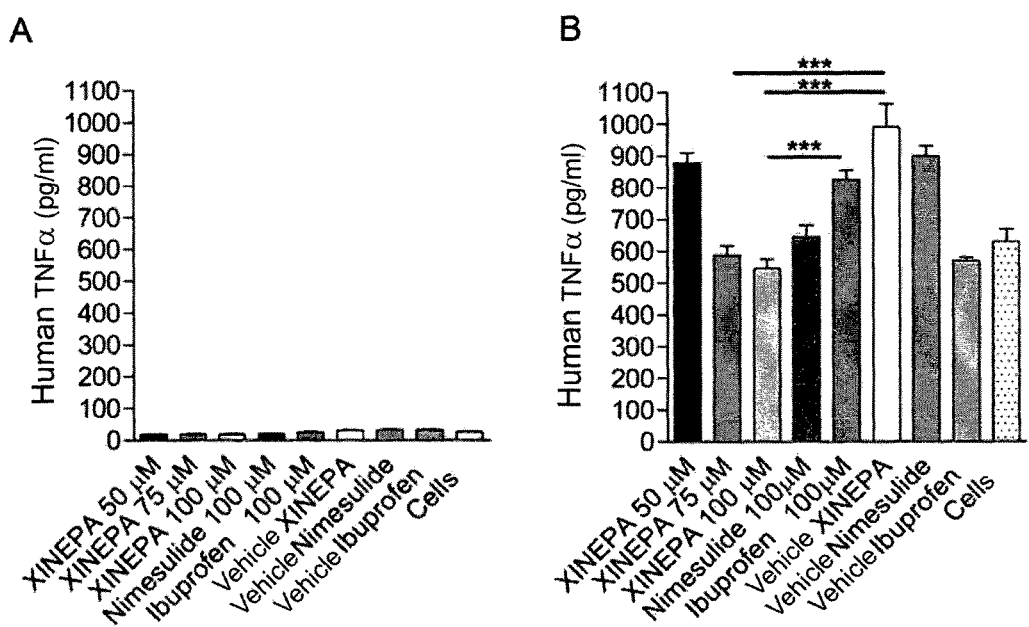
FIG. 2 is a representation of the results obtained in the ELISA assay 1a for quantifying TNFalpha in the culture medium of THP-1 monocytes differentiated as a result of pre-incubation with Xinepa and the various controls in the absence of inflammatory stimulus (A) or in the presence of inflammatory stimulus, i.e. incubation with LPS 1 μg/ml for 2 hours (B). (***=$p<0.001$)

The release of the pro-inflammatory cytokines TNFα, IL-1β and IL-6 in the culture medium by the differentiated THP-1 monocytes was evaluated both in the absence and in the presence of stimulation with LPS for 2 hours. The data obtained for TNFα are summarized in FIG. 2.

In the absence of inflammatory stimulus, production of TNFα was very low, but, as expected, it was amplified considerably by stimulation with LPS.

Incubation for 16 hours with Xinepa 75 µM and 100 µM caused a statistically significant reduction in the release of TNFα relative to the control condition (incubation with the Xinepa vehicle, white bar). Release of TNFα in the culture medium as a result of incubation with Xinepa 100 µM was significantly lower relative to the positive control nimesulide, which showed anti-inflammatory action, as expected. Incubation with ibuprofen, in contrast, did not cause any reduction in the release of TNFα relative to the control.

Figure 3:
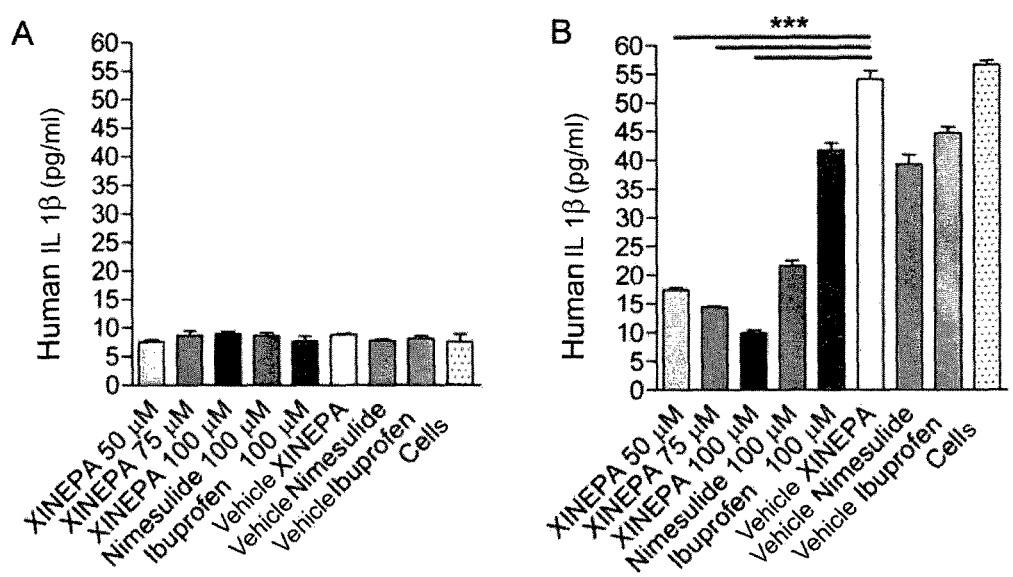
FIG. 3 is a representation of the results obtained in the ELISA assay 1a for quantifying IL-1beta in the culture medium of THP-1 monocytes differentiated as a result of pre-incubation with Xinepa and the various controls in the absence of inflammatory stimulus (A) or in the presence of inflammatory stimulus, i.e. incubation with LPS 1 μg/ml for 2 hours (B). (***=$p<0.001$)

The data relating to the quantification of IL-1β are summarized in FIG. 3. Just as for TNFα, quantification of IL-1β also showed a significant increase in release as a result of inflammatory stimulus with LPS, although less than the increase measured for TNFα. In this too, the effect was significantly better relative to the control at all the concentrations of Xinepa tested and comparable or better than that measured for nimesulide, which however was effective in reducing the release of IL-1β. Ibuprofen, in contrast, did not have any effect on release of IL-1β.

Figure 4:
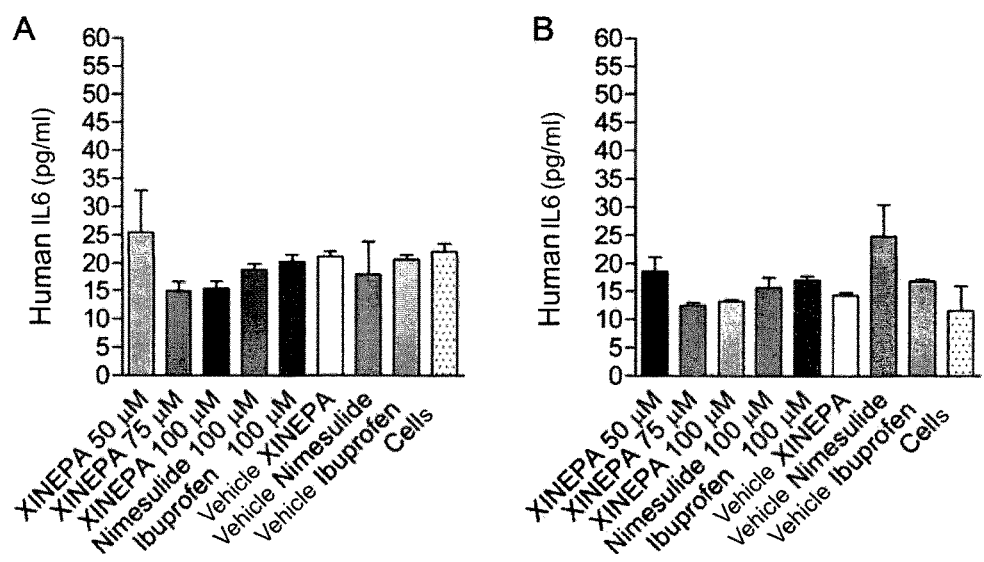
FIG. 4 is a representation of the results obtained in the ELISA assay 1a for quantifying IL-6 in the culture medium of THP-1 monocytes differentiated as a result of pre-incubation with Xinepa and the various controls in the absence of inflammatory stimulus (A) or in the presence of inflammatory stimulus, i.e. incubation with LPS 1 µg/ml for 2 hours (B). (***=p<0.001)

Data relating to quantification of IL-6 are summarized in FIG. 4. Release of IL-6 was not stimulated significantly by stimulation with LPS, and probably required longer incubation times.

Nuclear Translocation of NF-kB (Assay 1b)

Figure 5:
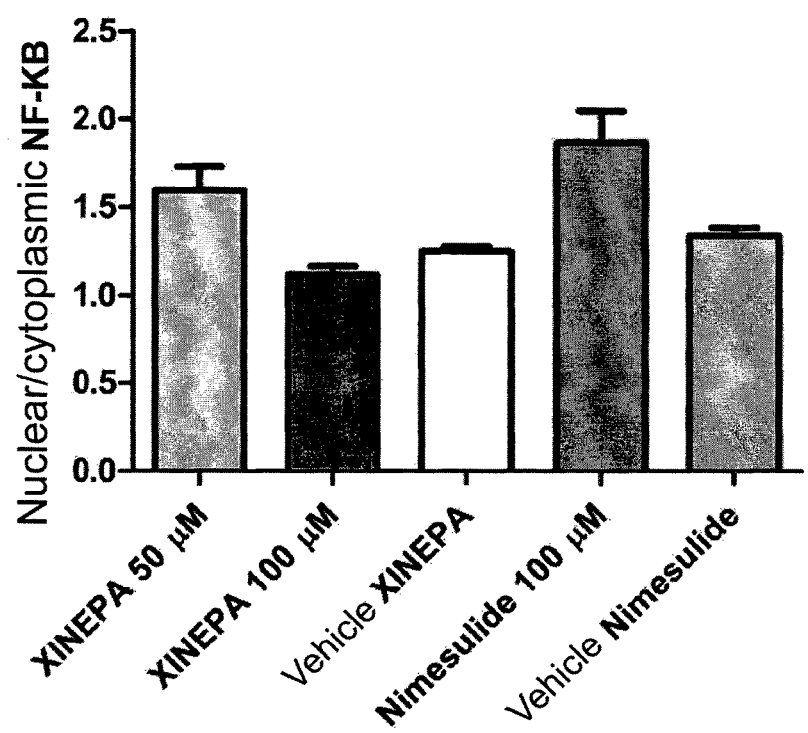
FIG. 5 is a representation of the results obtained in Assay 1b for quantifying the nuclear translocation of NF-kB.

Quantification of the nuclear translocation of NF-kB as a result of inflammatory stimulus with LPS, with or without pre-incubation with Xinepa, with nimesulide or with the respective negative controls did not detect a clearly antagonizing role of Xinepa on translocation of NF-kB to the nucleus (FIG. 5).

Evaluation of Intracellular Levels of ROS (Assay 2)

Figure 6:
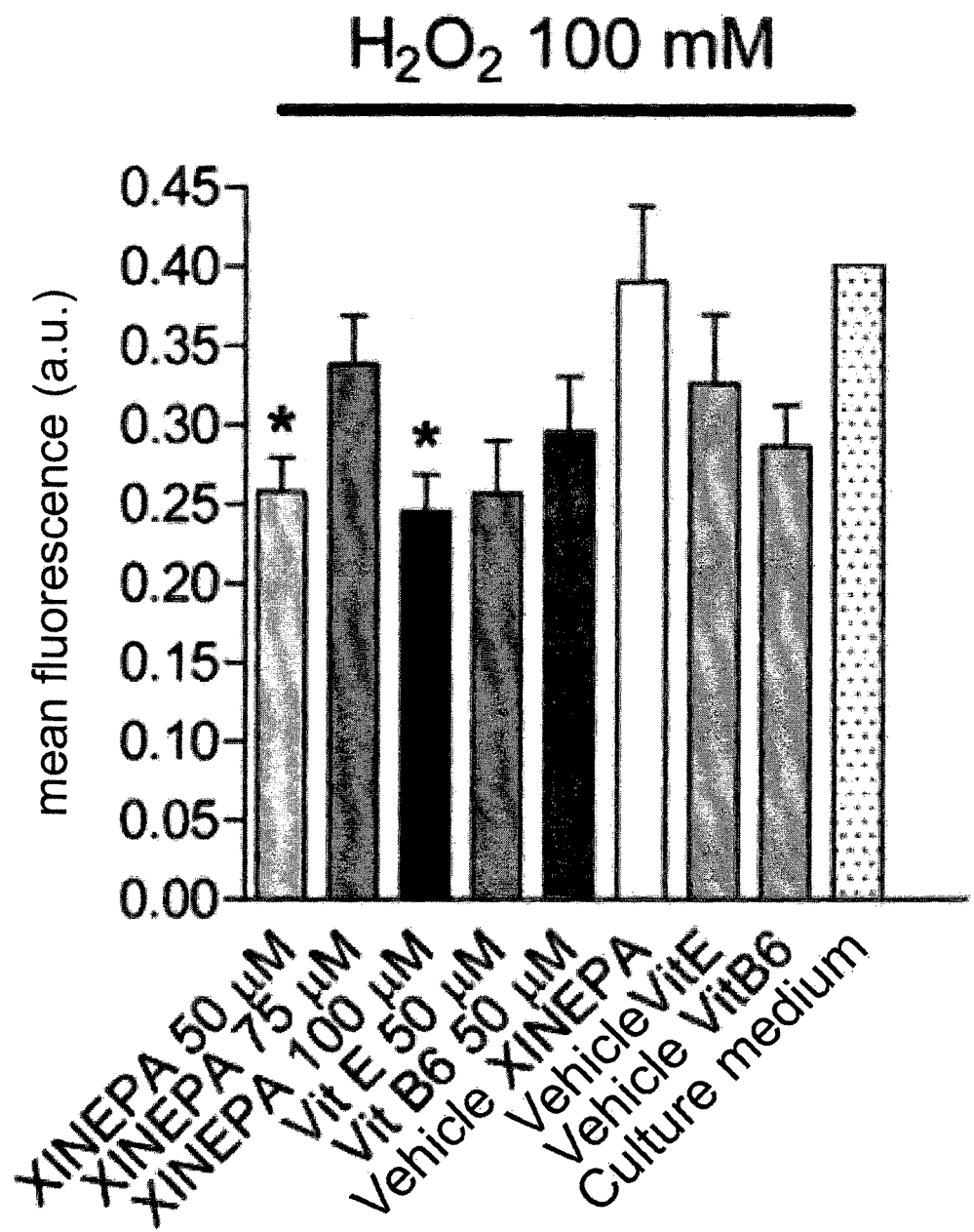
FIG. 6 is a representation of the results obtained in Assay 2 for quantifying the antioxidant activity of Xinepa; the THP-1 monocytes were incubated for about 16 hours with the compounds indicated in the figure and were then submitted to an inflammatory stimulus for 2 hours with $H_2O_2$ concomitantly with differentiation in serum-free medium. (*=p<0.05)

The antioxidant action of Xinepa is summarized in FIG. 6. Incubation overnight with Xinepa 50 or 75 µM led to greater resistance of THP-1 monocytes to the production of ROS as a result of stimulation with 100 mM $H_2O_2$ for 2 hours relative to incubation with the vehicle alone. Of the 2 positive controls tested, only vitamin E showed a partial antioxidant action in our system, although the average ROS levels were not significantly different from its control (incubation with vehicle only).

Conclusions

Xinepa demonstrated both anti-inflammatory properties and antioxidant properties in the cellular model of THP-1 human monocytes used for this study.

Example 2. Study of the Anti-Free-Radical Synergy Between the Components of a Dietary Supplement in Cell Cultures of Human Monocytes (THP-1)

The purpose of the assay is to evaluate the antioxidant activity of the individual components of the dietary supplement Xinepa and the synergy between them, by measuring its capacity for neutralizing the reactive oxygen species (ROS) in a cell line of human monocytes (THP-1). To identify the non-cytotoxic concentrations of the product in question, a colorimetric assay (MTT assay) was used as a preliminary test.

Table 2 below shows the composition of the product used in the assay in question.

TABLE 2

| Substance | mg/dose (one tablet) |
|---|---|
| *Curcuma* | 150.00 |
| Lipoic acid | 300.00 |
| Vitamin C | 125.00 |
| Vitamin E acetate | 9.00 |
| N-Acetyl-L-carnitine | 400.00 |
| Vitamin B1 | 6.25 |
| Vitamin B2 | 6.25 |
| Vitamin B6 | 6.25 |
| Vitamin B12 | 6.25 |

The individual components tested for investigating synergy are shown below:
COMPONENT A: *curcuma*
COMPONENT B: lipoic acid, vitamin C, vitamin E acetate
COMPONENT C: N-acetyl-L-carnitine Bearing in mind that the dietary supplement comes into contact with the gastrointestinal tract, it was presumed that at the level of the stomach the tablet might be dissolved by the action of the gastric juices in a volume of about 50 ml, producing a final concentration of the components equal to that given in Table 3 below.

Component C did not cause problems in dissolution in RPMI medium with addition of 10% fetal bovine serum (FBS), L-glutamine 2 mM and antibiotics (penicillin 100 IU/ml and streptomycin 100 μg/ml) (complete medium). In contrast, *curcuma* and lipoic acid, which have very low solubilities in aqueous solution, were dissolved beforehand in dimethylsulphoxide (DMSO) and then diluted in complete medium, in such a way that the percentage of solvent present was not greater than 0.2%, a concentration that is known to be non-cytotoxic.

TABLE 3

Concentration of the components of Xinepa assuming complete dissolution in 50 ml

| Component | Substance | mg/dose (one tablet) | Concentration (mg/ml)* |
|---|---|---|---|
| A | *Curcuma* | 150.00 | 3.00 |
| B | Lipoic acid | 300.00 | 6.00 |
|   | Vitamin C | 125.00 | 2.50 |
|   | Vitamin E acetate | 9.00 | 0.18 |
| C | N-Acetyl-L-carnitine | 400.00 | 8.00 |

Values relating to the individual components assuming a volume of 50 ml

Cell Cultures

The tests were conducted on THP-1 human monocytes (ATCC Number: TIB-202TM).

The THP-1 cells were cultured in complete medium (indicated above) and in conditions of complete sterility (at 37° C. with atmosphere with 5% $CO_2$).

Cytotoxicity Assay

The MTT assay is a colorimetric cytotoxicity assay that makes it possible to test cellular proliferation and vitality based on the efficiency of mitochondrial respiration. MTT (3-(4,5-dimethylthiazol-2-yl)-2,5-diphenyl tetrazolium bromide) is a tetrazolium salt that is reduced by the highly reducing environment in the mitochondria of living cells by the action of mitochondrial dehydrogenase. Reduction of MTT causes formation of crystals of formazan that give the characteristic purple coloration to the mitochondria of living cells. In contrast, in dead cells or cells in distress, and therefore with inactive mitochondria, MTT will not be reduced, with a consequent less intense or absent purple coloration. Thus, although it is a test that evaluates cellular respiration, the MTT assay is considered to be an excellent method for determining cellular vitality. For this reason it was used as a preliminary analysis for determining the non-cytotoxic concentrations of the individual components of the dietary supplement Xinepa and mixture thereof for the purpose of finding those useful for assay of ROS.

As preparation for the test, the cells were sown uniformly in 96-well plates at a density of $5 \times 10^4$ cells per well and incubated at 37° C., with 5% $CO_2$, and simultaneously, the cells were treated following serial dilutions (1:2) in order to identify the maximum non-cytotoxic concentration for each component.

The treatment was carried out for 24 hours. At the end, after brief washing in PBS, 20 μl of MTT (stock 5 mg/ml) in PBS was added to the THP-1 cells for 2 hours at 37° C. At the end of the incubation time, after removal from the medium and washing in PBS, 100 μl of DMSO was added for solubilization of the formazan crystals. Spectrophotometric reading was performed with a microplate reader (Tecan Sunrise) at a wavelength of 570 nm. The cellular vitality was calculated by measuring the optical density of the concentrations tested relative to the control (untreated cells).

ROS Assay

The antioxidant activity of the individual components and synergy between them was evaluated as efficiency of neutralization of the ROS produced by the THP-1 cells after application of an oxidizing agent: hydrogen peroxide ($H_2O_2$) at a concentration of 100 μM. The ROS were measured by the method described in Boulton S., Anderson A., Swalwell J., et al., 2011 Implications of using the fluorescent probes, dihydrorhodamine 123 and 2',7'-dichlorodihydrofluorescein diacetate, for the detection of UV-A induced reactive oxygen species. Free Radical Research; 45: 115-122, that makes use of the transformation of dihydro-2'-7'-dichlorofluorescein diacetate ($H_2DCF$-DA) into a fluorescent derivative in the presence of ROS. Specifically, the $H_2DCF$-DA probe penetrates into the cells where it is diesterified into a non-fluorescent form ($H_2DCF$) by the endogenous esterases. In the presence of the intracellular ROS, $H_2DCF$ is oxidized to a fluorescent compound, dichlorofluorescein (DCF). The DCF produced is then quantified by reading with a flow cytometer and is proportional to the quantity of ROS present in the sample under examination.

As preparation for the assay, the THP-1 cells were sown uniformly and treated with the maximum concentrations found to be non-cytotoxic in the MTT assay in Petri dishes at a density of $3.5 \times 10^5$ cells in 3 ml of complete medium and were incubated at 37° C., with 5% $CO_2$.

After 18 hours since seeding, the complete medium was removed and was replaced with serum-free medium for further incubation for 2 hours in the presence of $H_2O_2$ (100 μM).

After this, the cells were washed with PBS and incubated with $H_2DCF$-DA solution, previously dissolved in ethanol at a concentration of 1 mg/100 μl, for 30 min (5 μM) in a thermostat with $CO_2$ at 37° C.

After removal of the $H_2DCF$-DA solution, the cells were washed, collected and the fluorescence of the DCF was measured by analysis with a Coulter Epics XL flow cytofluorimeter. At least ten thousand cells were analysed for each sample and the mean fluorescence intensity was quantified by the XL2 software of the instrument.

Results

The results obtained are given in tabular and graphical form containing the measurements of cellular vitality (MTT assay) and possible reduction of the ROS produced as a result of treatment with the individual components of the product Xinepa or by their synergy. In this case the parameter taken into consideration is the MFI (Mean Fluorescence Intensity), i.e. the geometric mean of the fluorescence intensity of DCF, which is proportional to the quantity of ROS.

The values shown represent mean±SD of at least two experiments conducted singly. For statistical analysis, in view of the small number of data to be analysed, the Kruskal-Wallis test was selected, a non-parametric method performed on sorted data using an Excel spreadsheet generated by Prof. J. H. McDonald (Delaware University (http://www.socscistatistics.com/Default.aspx).

Cellular Vitality

THP-1 cells were incubated (treatment time 24 hours) with different concentrations of the individual components in order to identify the concentrations that do not cause cellular mortality greater than 30%. From the results obtained, the individual components showed a varying range of cytotoxicity; Table 4 gives the range tested for each component (5 concentrations with successive dilutions 1:2) within which it is possible to identify the maximum non-cytotoxic concentration.

TABLE 4

Concentration range tested for each substance.

| COMPONENT | SUBSTANCE | RANGE TESTED (mg/ml) |
|---|---|---|
| A | *Curcuma* | 0.03-0.0019 |
| B | Lipoic acid | 0.75-0.0469 |
|   | Vitamin C | 0.313-0.0196 |
|   | Vitamin E acetate | 0.0225-0.0014 |
| C | N-Acetyl-L-carnitine | 4-0.25 |

Figure 7:
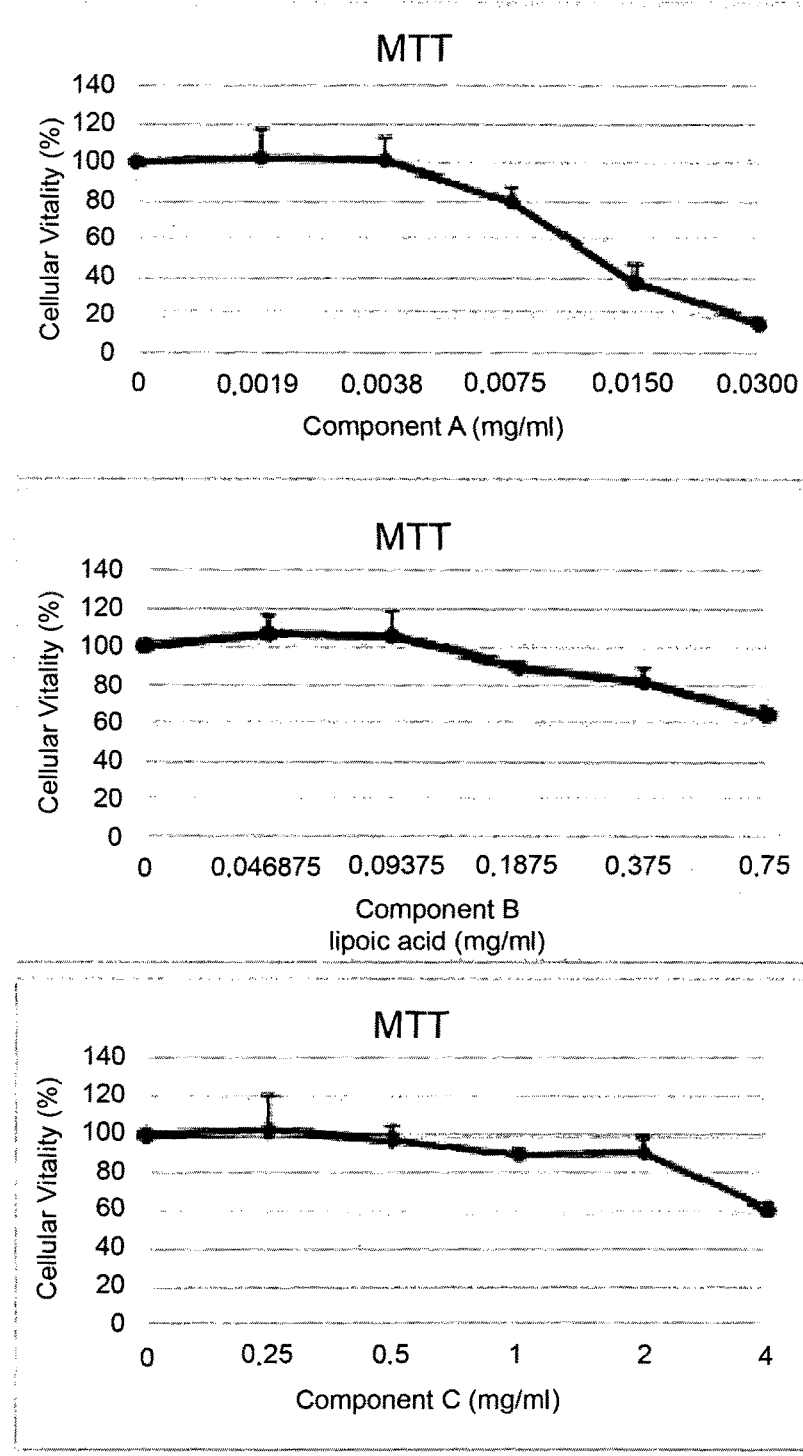
FIG. 7 is a graph showing cellular vitality expressed as a percentage relative to the control (untreated cells) as a result of 24-hour treatment of THP-1 cells with the three components of the dietary supplement Xinepa. Component A (blue)=*curcuma*; Component B (red)=lipoic acid (reference concentrations given on the x axis), vitamin C and vitamin E acetate; Component C (green)=N-acetyl-L-carnitine (n=2; repetitions=3)

FIG. 7 shows a graph relating to the cellular vitality of the three components, expressed as a percentage relative to the control (untreated cells), as a function of increasing concentrations of the components A, B and C.

Table 5 gives the data expressed as a percentage. The minimum vitalities considered acceptable are shown in red.

As can be seen from Table 6, the maximum non-cytotoxic concentration of the ingredients of the supplement in comparison with the cell line of human monocytes used is of varying orders of magnitude below the concentrations of the components present in the dietary supplement dissolved in 50 ml.

TABLE 6

Concentration of each component of the tablet dissolved in 50 ml and maximum non-cytotoxic concentration.

| COMPONENT | mg/tablet | mg/ml in final 50 ml | Maximum non-cytotoxic concentration (mg/ml) | DF |
|---|---|---|---|---|
| *Curcuma* | 150 | 3 | 0.0075 | 400 |
| Lipoic acid | 300 | 6 | 0.3750 | 16 |
| Vitamin C | 125 | 2.5 | 0.1565 | 16 |
| Vitamin E acetate | 9 | 0.18 | 0.0113 | 16 |
| N-Acetyl-L-carnitine | 400 | 8 | 2 | 4 |

DF: dilution factor applied

For investigating the synergy between the various components, it was necessary to take into account the high cytotoxicity of *curcuma*; the first non-cytotoxic concentration equal to 0.0075 mg/ml is in fact 400 times lower than the 3 mg/ml obtained on dissolving the tablet in 50 ml of solvent. This value is very close to the non-cytotoxic concentration found for curcumin (Sigma, commercial) in the article Hsu H. Y., Chu L., Hua K., et al., 2008 Haem oxygenase-1 mediates the anti-inflammatory effect on curcumin within LPS-stimulated human monocytes. Cell Physiol; 215: 603-612. This relates to a study conducted on the same experimental model (the THP-1 cell line): 10 µM compared to 20 µM of that tested in our experiments.

Figure 8:
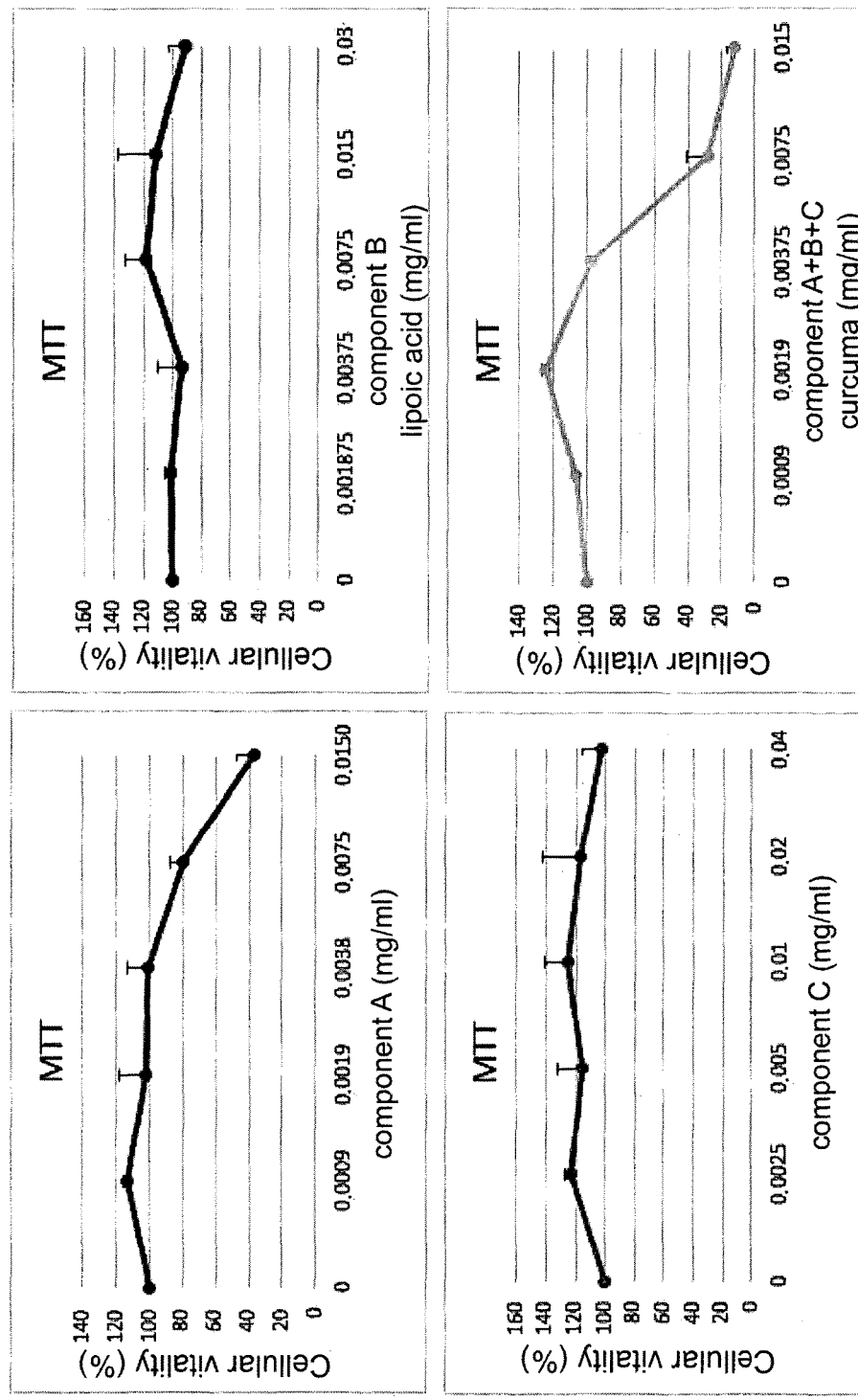
FIG. 8 is a graph showing cellular vitality expressed as a percentage relative to the control (untreated cells) as a result of 24-hour treatment of THP-1 cells with the three individual components (A–B–C) and as a mixture (A+B+C) of the dietary supplement Xinepa. Component A (blue)=*curcuma*; Component B (red)=lipoic acid (reference concentrations given on the x axis), vitamin C and vitamin E acetate; Component C (green)=N-acetyl-L-carnitine. Component A+B+C (orange) (n=2; repetitions=3)

To evaluate the possible cytotoxicity of the mixture, we tested successive dilutions of each component (A–B–C) and of the mixture (A+B+C), maintaining in the latter the proportions in which the various components are present in the dietary supplement, as can be seen in Table 7 and FIG. 8.

TABLE 5

Cellular vitality expressed as a percentage for each component.

| Component A | | | | | | |
|---|---|---|---|---|---|---|
| *Curcuma* (mg/ml) | 0 | 0.0019 | 0.0038 | 0.0075 | 0.015 | 0.03 |
| Cellular vitality (%) | 100 | 102.093 | 100.571 | 80.195 | 37.675 | 15.814 |
| Component B | | | | | | |
| Lipoic acid (mg/ml) | 0 | 0.0469 | 0.0938 | 0.1875 | 0.375 | 0.75 |
| Vitamin C (mg/ml) | 0 | 0.0196 | 0.0391 | 0.0783 | 0.1565 | 0.313 |
| Vitamin E acetate (mg/ml) | 0 | 0.0014 | 0.0028 | 0.0056 | 0.0113 | 0.0225 |
| Cellular vitality (%) | 100 | 106.656 | 105.528 | 90.064 | 81.541 | 64.407 |
| Component C | | | | | | |
| N-Acetyl-L-carnitine (mg/ml) | 0 | 0.25 | 0.5 | 1 | 2 | 4 |
| Cellular vitality (%) | 100 | 102.221 | 97.615 | 90.355 | 91.422 | 60.848 |

TABLE 7

Concentrations (mg/ml) tested for the individual components and for the mixture, starting from the most concentrated (column number 5) and effecting scalar dilutions 1:2.

| COMPONENT | | 1 | 2 | 3 | 4 | 5 |
|---|---|---|---|---|---|---|
| A | Curcuma | 0.0009 | 0.0019 | 0.00375 | 0.0075 | 0.015 |
| B | Lipoic acid | 0.001875 | 0.00375 | 0.0075 | 0.015 | 0.03 |
|  | Vitamin C | 0.0008 | 0.0016 | 0.00313 | 0.00625 | 0.0125 |
|  | Vitamin E acetate | 0.00006 | 0.000113 | 0.000225 | 0.00045 | 0.0009 |
| C | N-Acetyl-L-carnitine | 0.0025 | 0.005 | 0.01 | 0.02 | 0.04 |

FIG. 8 shows a graph relating to the cellular vitality of the individual components and of the mixture, expressed as a percentage relative to the control (untreated cells), as a function of increasing concentrations of the components A, B and C and of the mixture (A+B+C).

As can be seen from the graph, the two components B and C are not found to be cytotoxic at any of the concentrations tested (cellular vitality greater than 70%). Specifically, it can be seen that the same concentration that proved non-cytotoxic for component A (0.0075 mg/ml) proved to be so when added to the other two components, bringing the first non-cytotoxic concentration (cellular vitality=97.89%) of *curcuma* to 0.00375 mg/ml. Table 8 shows the relative concentrations of components B and C at the same point.

TABLE 8

Non-cytotoxic concentrations reported for each component when tested together (A + B + C).

| A + B + C | Non-cytotoxic concentration (mg/ml) |
|---|---|
| Curcuma | 0.00375 |
| Lipoic acid | 0.00750 |
| Vitamin C | 0.00313 |
| Vitamin E acetate | 0.00023 |
| N-Acetyl-L-carnitine | 0.01000 |

Antioxidant Activity

The antioxidant action of the individual components of Xinepa and the synergy was evaluated by measuring the ROS produced as a result of treatment with $H_2O_2$. The parameter considered is MFI, mean fluorescence intensity, i.e. the geometric mean of the fluorescence intensity of the cells in which H2DCF-DA has been transformed into the fluorescein-treated DCF form, which is proportional to the amount of ROS per sample. The baseline fluorescence was evaluated using THP-1 cells not incubated with $H_2DCF-DA$ (blank); cells treated with $H_2O_2$ in serum-free medium for 2 hours were used as positive control. Cells pre-treated (24 h) with the individual components or with the mixture were then incubated with $H_2O_2$ in serum-free medium for 2 hours and processed for investigation of ROS.

Figure 9:
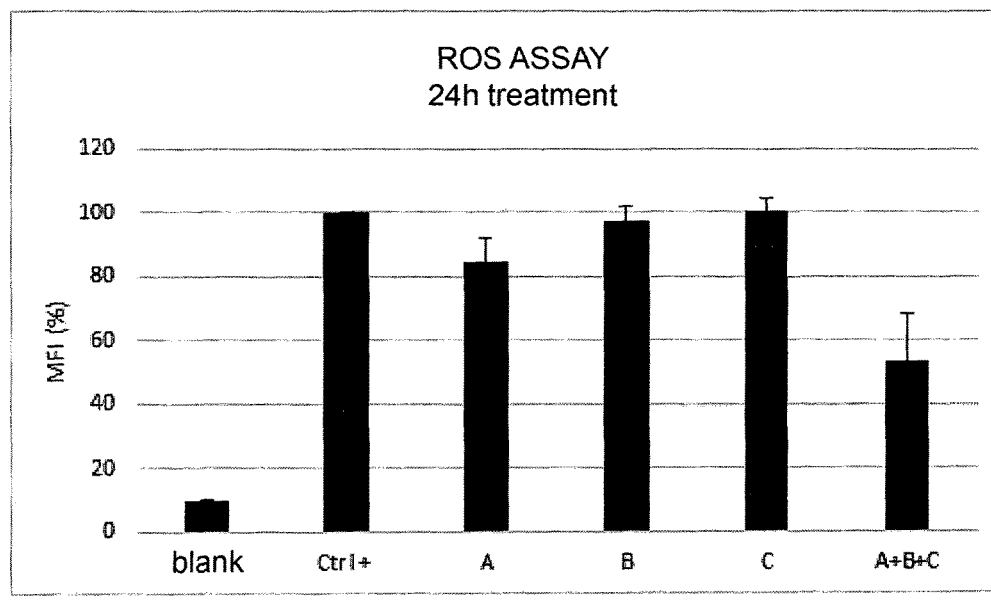
FIG. 9 shows quantitative analysis of the mean fluorescence intensity (MFI) expressed as a percentage relative to the positive control emitted by THP-1 cells after treatment (24 hours) with the individual components A, B and C or the mixture A+B+C (at least n=2; repetitions=1). * p≤0.05 ** p≤0.01: significance relative to the positive control (Ctrl+)

FIG. 9 gives the results expressed as a percentage, relative to the positive control (expressed as 100%).

The results obtained demonstrate that component A (*curcuma*) tested at a concentration of 0.00375 mg/ml causes a reduction in the production of ROS after 24-hour treatment and then treatment with $H_2O_2$ equal to 15.15%. This reduction was statistically significant (* p=0.05) relative to the control. Following treatment with components B and C at the concentrations indicated in Table 7, the levels of ROS are comparable to those of the positive control (Ctrl+).

These data are in agreement with data in the literature: the antioxidant activity of *curcuma* has in fact been demonstrated in the same cell line. However, the antioxidant activity of the other components in THP-1 cells has not been reported in the literature.

The data relating to the antioxidant activity of the three components combined (A+B+C) were very interesting; as shown in the graph, the decrease in the production of ROS after 24-hour treatment and then treatment with $H_2O_2$ is equal to 48.62%. This reduction was statistically significant (** p≤0.01) both relative to the control and relative to components A, B and C taken individually. In fact the decrease in the production of ROS is far greater than that recorded for the components taken individually, indicating a synergistic effect equal to three times the individual value for *curcuma*.

Conclusions

The results obtained show that, together, the components A, B and C of the product Xinepa cause a decrease in reactive oxygen species. This reduction is statistically significant both relative to the control and relative to the individual components (more than threefold relative to the individual components). Thus, synergy in anti-free-radical activity has been demonstrated. Specifically, the three components investigated that constitute Xinepa are: *curcuma*, lipoic acid, vitamin C, vitamin E acetate and N-acetyl-L-carnitine. These were tested at non-cytotoxic concentrations, maintaining the proportions present in the dietary supplement.

Example 3. Investigation of the Anti-Inflammatory Synergy Between the Components of a Dietary Supplement in Cell Cultures of Human Monocytes (THP-1)

The purpose of the assay is to evaluate the anti-inflammatory potential of the individual components of the dietary supplement Xinepa and possible synergy between them, by measuring the levels of IL1-β and TNFα, two cytokines implicated in the inflammatory processes and immune system processes, in a cell line of human monocytes (THP-1). To ascertain the non-cytotoxic concentrations of the product in question, a colorimetric assay (MTT assay) was used as a preliminary test.

Table 9 below shows the composition of the product used in the assay in question.

TABLE 9

| Substance | mg/dose (1 tablet) |
|---|---|
| Curcuma | 150.00 |
| Lipoic acid | 300.00 |
| Vitamin C | 125.00 |
| Vitamin E acetate | 9.00 |
| N-Acetyl-L-carnitine | 400.00 |

TABLE 9-continued

| Substance | mg/dose (1 tablet) |
|---|---|
| Vitamin B1 | 6.25 |
| Vitamin B2 | 6.25 |
| Vitamin B6 | 6.25 |
| Vitamin B12 | 6.25 |

The following individual components were investigated:
COMPONENT A: *curcuma*
COMPONENT B: lipoic acid, vitamin C, vitamin E acetate
COMPONENT C: N-acetyl-L-carnitine Bearing in mind that the dietary supplement comes into contact with the gastrointestinal tract, it was assumed that in the stomach the tablet might be dissolved by the action of the gastric juices in a volume of about 50 ml, leading to a final concentration of the components equal to that given in Table 10.

Component C did not cause problems of dissolution in RPMI medium with addition of 10% of fetal bovine serum (FBS), L-glutamine 2 mM and antibiotics (penicillin 100 IU/ml and streptomycin 100 μg/ml) (complete medium). In contrast, *curcuma* and lipoic acid, which have very low solubilities in aqueous solution, were dissolved beforehand in dimethylsulphoxide (DMSO) and then diluted in complete medium, in such a way that the percentage of solvent present was not greater than 0.2%, a concentration that is known to be non-cytotoxic.

TABLE 10

Concentration of the components of Xinepa assuming complete dissolution in 50 ml.

| Component | Substance | mg/dose (one tablet) | Concentration (mg/ml)* |
|---|---|---|---|
| A | *Curcuma* | 150.00 | 3.00 |
| B | Lipoic acid | 300.00 | 6.00 |
|   | Vitamin C | 125.00 | 2.50 |
|   | Vitamin E acetate | 9.00 | 0.18 |
| C | N-Acetyl-L-carnitine | 400.00 | 8.00 |

Values relating to the individual components assuming a volume of 50 ml

Cell Cultures

The tests were conducted on THP-1 human monocytes (ATCC Number: TIB-202™).

The THP-1 cells were cultured in complete medium (indicated above) and in conditions of complete sterility (at 37° C. with atmosphere at 5% $CO_2$).

Cytotoxicity Assay

The MTT assay is a colorimetric cytotoxicity assay that makes it possible to test cellular proliferation and vitality based on the efficiency of mitochondrial respiration. MTT (3-(4,5-dimethylthiazol-2-yl)-2,5-diphenyl tetrazolium bromide) is a tetrazolium salt that is reduced by the highly reducing environment in the mitochondria of living cells by the action of mitochondrial dehydrogenase. Reduction of MTT leads to formation of crystals of formazan that impart the characteristic purple coloration to the mitochondria of living cells. In contrast, in dead cells or cells in distress, which therefore have inactive mitochondria, MTT will not be reduced, with a consequent less intense or absent purple coloration (Mosmann T., 1983 Rapid colorimetric assay for cellular growth and survival: application to proliferation and cytotoxicity assays. J Immunol Methods.; 65: 55-63). Thus, although it is a test that evaluates cellular respiration, the MTT assay is regarded as an excellent method for determining cellular vitality. For this reason, it was used as a preliminary analysis for determining the non-cytotoxic concentrations of the individual components of the dietary supplement Xinepa and of a mixture thereof for the purpose of obtaining those that are useful for assay of ROS.

As preparation for the test, the cells were sown uniformly in 96-well plates at a density of $5 \times 10^4$ cells per well and incubated at 37° C., with 5% $CO_2$ and at the same time the cells were treated with serial dilutions (1:2) in order to identify the maximum non-cytotoxic concentration for each component.

The treatment was carried out for 24 hours. At the end, after brief washing in PBS, 20 μl of MTT (stock 5 mg/ml) in PBS was added to the THP-1 cells for 2 hours at 37° C. At the end of the incubation time, after removal from the medium and washing in PBS, 100 μl of DMSO was added to dissolve the formazan crystals. Spectrophotometric reading was performed with a microplate reader (Tecan Sunrise) at a wavelength of 570 nm. The cellular vitality was calculated by measuring the optical density of the concentrations tested relative to the control (untreated cells).

Analysis of Anti-Inflammatory Activity

Possible anti-inflammatory activity of the individual components and synergy between them in THP-1 cells was evaluated after 24 hours of treatment and stimulation with a known pro-inflammatory agent (LPS), measuring expression of IL-1β and TNFα using an ELISA kit (Thermo Fisher Scientific, Inc.).

As preparation for the test, the THP-1 cells were sown uniformly in a 96-well plate at a density of $5 \times 10^4$ cells/well and treated with the maximum concentrations found to be non-cytotoxic in the MTT assay; untreated cells were used as negative control. Treatment was carried out at 37° C. at 5% $CO_2$ for 20 h; then the sample was stimulated with LPS (component of the bacterial outer membrane, considered to be an inflammatory agent) for 4 hours.

At the end of the treatment, the supernatants were collected and used for coating a pretreated ELISA plate, supplied with the kit.

For analysis of the expression of both markers under examination (IL-1β and TNFα), a special kit is used that is based on the "sandwich" ELISA system in which a 96-well plate is coated with a monoclonal antibody specific to the particular cytokine.

The standards, prepared on the basis of the instructions in the protocol and used for constructing the calibration curve, and the samples are added to the wells and the cytokine of interest binds the capture antibody immobilized on the bottom of the well. Next, the biotinylated anti-cytokine antibody is added to the wells so that the biotinylated antibody-antigen-antibody "sandwich" is formed. This is followed by horseradish peroxidase conjugated to streptavidin and a solution of tetramethylbenzidine (TMB) which, reacting with the peroxide, produces a compound coloured blue, the intensity of which is proportional to the amount of cytokine present. Addition of a solution of sulphuric acid turns the colour of the solution from blue to yellow, blocking the reaction and allowing accurate reading of the absorbance of the samples at 450 nm.

The absorbance was then read at 450 and 550 nm using a microplate reader (Tecan Sunrise). The values obtained from the reading at 550 nm were subtracted from those at 450 nm to correct the optical imperfections of the microplate.

Statistical Analysis

In view of the small number of data to be analysed, a non-parametric method of analysis was used, suitable for a non-normal (non-Gaussian) distribution of the values. For evaluating the data presented in this report, the Kruskal-Wallis test was therefore selected. The Kruskal-Wallis test is performed on sorted data and is useful for comparing three or more groups, to evaluate whether the median ranks of the variables measured are the same in all the groups.

To perform the test, an Excel spreadsheet was used, generated by Prof. J. H. McDonald (Delaware University), available in the 3rd online edition of his Manual of Biological Statistics (biostathandbook.com/kruskalwallis).

Results

The results obtained are given in tabular and graphical form containing the measurements of cellular vitality (MTT assay) and possible anti-inflammatory activity as a result of treatment with the individual components of the product Xinepa or from synergy thereof.

Cellular Vitality

THP-1 cells were incubated (treatment time 24 hours) with different concentrations of the individual components for the purpose of identifying the concentrations that do not cause cellular mortality greater than 30%. From the results obtained, the individual components showed a varying range of cytotoxicity; Table 11 gives the range tested for each component (5 concentrations with successive dilutions 1:2) within which it is possible to identify the maximum non-cytotoxic concentration.

TABLE 11

Concentration range tested for each substance.

| COMPONENT | SUBSTANCE | RANGE TESTED (mg/ml) |
|---|---|---|
| A | *Curcuma* | 0.03-0.0019 |
| B | Lipoic acid | 0.75-0.0469 |
|   | Vitamin C | 0.313-0.0196 |
|   | Vitamin E acetate | 0.0225-0.0014 |
| C | N-Acetyl-L-carnitine | 4-0.25 |

Figure 10:
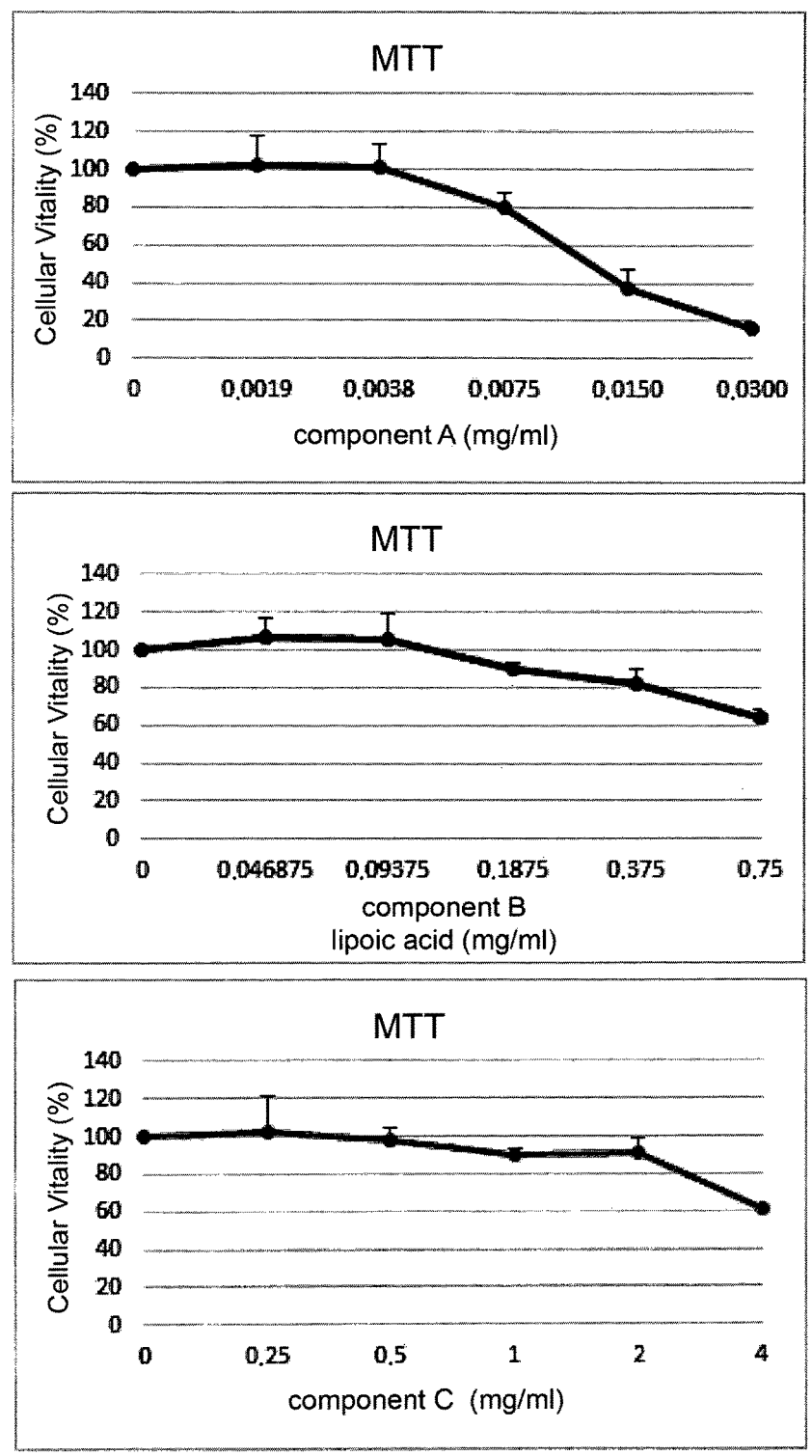
FIG. 10 is a graph showing cellular vitality expressed as a percentage relative to the control (untreated cells) as a result of 24-hour treatment of THP-1 cells with the three components of the dietary supplement Xinepa. Component A (blue)=*curcuma*; Component B (red)=lipoic acid (reference concentrations given on the x axis), vitamin C and vitamin E acetate; Component C (green)=N-acetyl-L-carnitine (n=2; repetitions=3)

FIG. 10 shows the graph relating to the cellular vitality of the three components, expressed as a percentage relative to the control (untreated cells), as a function of increasing concentrations of the components A, B and C.

Table 12 gives the data expressed as a percentage. The minimum vitalities considered acceptable are in red.

As can be seen from Table 13, the maximum non-cytotoxic concentration of the ingredients of the supplement with respect to the cell line of human monocytes used is of various orders of magnitude lower than the concentrations of the components present in the dietary supplement dissolved in 50 ml.

TABLE 13

Concentration of each component of the tablet dissolved in 50 ml and maximum non-cytotoxic concentration.

| COMPONENT | mg/tablet | mg/ml in final 50 ml | Maximum non-cytotoxic concentration (mg/ml) | DF |
|---|---|---|---|---|
| *Curcuma* | 150 | 3 | 0.0075 | 400 |
| Lipoic acid | 300 | 6 | 0.3750 | 16 |
| Vitamin C | 125 | 2.5 | 0.1565 | 16 |
| Vitamin E acetate | 9 | 0.18 | 0.0113 | 16 |
| N-Acetyl-L-carnitine | 400 | 8 | 2 | 4 |

DF: dilution factor applied

For investigating the synergy between the various components, it was necessary to take into account the high cytotoxicity of *curcuma*; the first non-cytotoxic concentration, equal to 0.0075 mg/ml, is in fact 400 times lower than the 3 mg/ml obtained on dissolving the tablet in 50 ml of solvent. This value is very close to the non-cytotoxic concentration found for curcumin (Sigma, commercial) in a work by Hsu et al. (Hsu H. Y. et al., 2008) conducted on the same experimental model (THP-1 cell line): 10 µM compared to 20 µM of that tested in the experiments of the present inventors.

Figure 11:
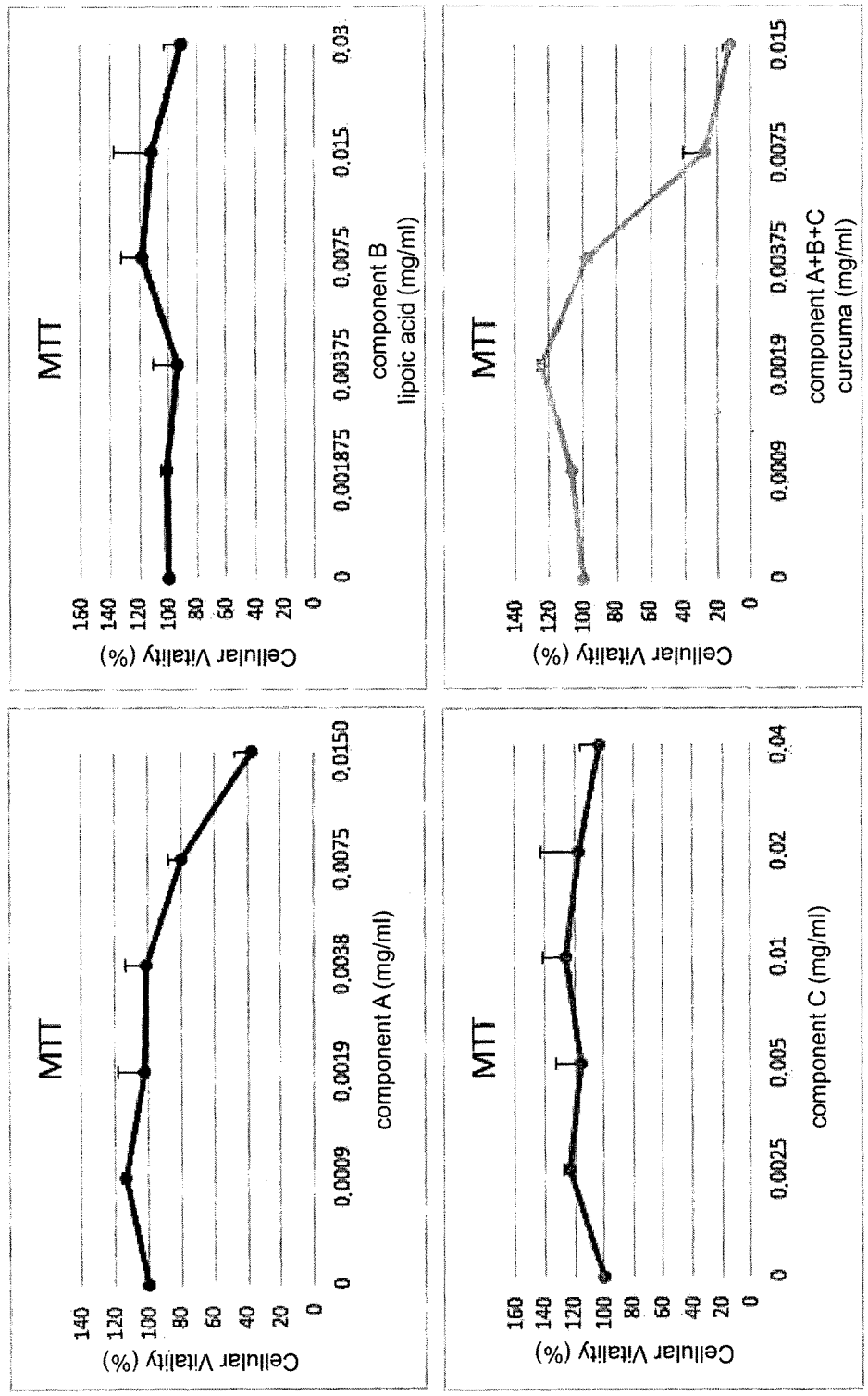
FIG. 11 is a graph showing cellular vitality expressed as a percentage relative to the control (untreated cells) as a result of 24-hour treatment of THP-1 cells with the three individual components (A–B–C) and as a mixture (A+B+C) of the dietary supplement Xinepa. Component A (blue)=*curcuma*; Component B (red)=lipoic acid (reference concentrations given on the x axis), vitamin C and vitamin E acetate; Component C (green)=N-acetyl-L-carnitine. Component A+B+C (orange) (n=2; repetitions=3)

To evaluate possible cytotoxicity of the mixture, we tested successive dilutions of each component (A–B–C) and of the mixture (A+B+C), maintaining in the latter the proportions in which the various components are present in the dietary supplement, as can be seen in Table 14 and FIG. 11.

TABLE 12

Cellular vitality expressed as a percentage for each component.

| Component A | | | | | | |
|---|---|---|---|---|---|---|
| *Curcuma* (mg/ml) | 0 | 0.0019 | 0.0038 | 0.0075 | 0.015 | 0.03 |
| Cellular vitality (%) | 100 | 102.093 | 100.571 | 80.195 | 37.675 | 15.814 |
| Component B | | | | | | |
| Lipoic acid (mg/ml) | 0 | 0.0469 | 0.0938 | 0.1875 | 0.375 | 0.75 |
| Vitamin C (mg/ml) | 0 | 0.0196 | 0.0391 | 0.0783 | 0.1565 | 0.313 |
| Vitamin E acetate (mg/ml) | 0 | 0.0014 | 0.0028 | 0.0056 | 0.0113 | 0.0225 |
| Cellular vitality (%) | 100 | 106.656 | 105.528 | 90.064 | 81.541 | 64.407 |
| Component C | | | | | | |
| N-Acetyl-L-carnitine (mg/ml) | 0 | 0.25 | 0.5 | 1 | 2 | 4 |
| Cellular vitality (%) | 100 | 102.221 | 97.615 | 90.355 | 91.422 | 60.848 |

TABLE 14

Concentrations (mg/ml) tested for the individual components and for the mixture, starting from the most concentrated (column number 5) and effecting scalar dilutions 1:2.

| COMPONENT | | 1 | 2 | 3 | 4 | 5 |
|---|---|---|---|---|---|---|
| A | Curcuma | 0.0009 | 0.0019 | 0.00375 | 0.0075 | 0.015 |
| B | Lipoic acid | 0.001875 | 0.00375 | 0.0075 | 0.015 | 0.03 |
|   | Vitamin C | 0.0008 | 0.0016 | 0.00313 | 0.00625 | 0.0125 |
|   | Vitamin E acetate | 0.00006 | 0.000113 | 0.000225 | 0.00045 | 0.0009 |
| C | N-Acetyl-L-carnitine | 0.0025 | 0.005 | 0.01 | 0.02 | 0.04 |

FIG. 11 shows the graph relating to the cellular vitality of the individual components and of the mixture, expressed as a percentage relative to the control (untreated cells), as a function of increasing concentrations of the components A, B and C and of the mixture (A+B+C).

As can be seen from the graph, the two components B and C are not found to be cytotoxic at any of the concentrations tested (cellular vitality above 70%). Specifically, it can be seen that the same concentration that proved non-cytotoxic for component A (0.0075 mg/ml) was non-cytotoxic when added to the other two components, bringing the first non-cytotoxic concentration (cellular vitality=97.89%) of *curcuma* to 0.00375 mg/ml. Table 15 shows the relative concentrations of components B and C at the same point.

TABLE 15

Non-cytotoxic concentrations reported for each component when tested together (A + B + C).

| A + B + C | Non-cytotoxic concentration (mg/ml) |
|---|---|
| Curcuma | 0.00375 |
| Lipoic acid | 0.00750 |
| Vitamin C | 0.00313 |
| Vitamin E acetate | 0.00023 |
| N-Acetyl-L-carnitine | 0.01000 |

Anti-Inflammatory Activity

The anti-inflammatory activity of the individual components of Xinepa and the synergy were evaluated by measuring two cytokines involved in the inflammatory and immune process.

The two markers analysed are IL-1β and TNFα, both of which are able to induce expression of other pro-inflammatory mediators and are implicated in the development of neuropathic pain; for these reasons, they were selected for analysing the anti-inflammatory activity of the components of Xinepa, with, as pathological target, neuropathic pain from trauma or from an inflammatory effect.

Evaluation of Expression of IL-1β

The possible anti-inflammatory action of the individual components of Xinepa and the possible synergy were evaluated by measuring the levels of IL-1β following stimulation with LPS. The negative control is represented by cells that were not treated and not stimulated; cells pre-treated (20 h) with the individual components or with the mixture were incubated with LPS for 4 hours and the supernatant was collected for evaluating the interleukin levels.

Figure 12:
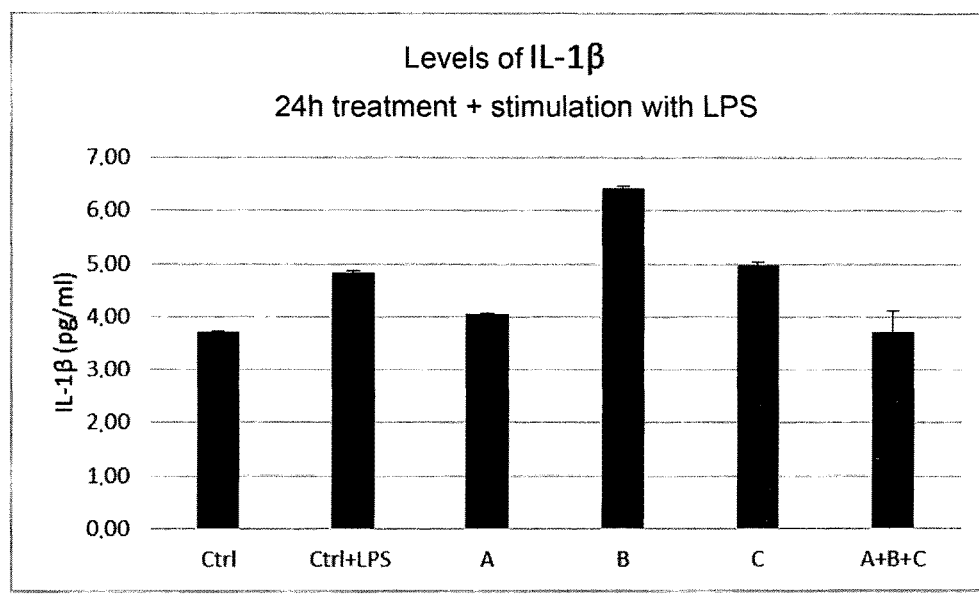
FIG. 12 is a graph showing the effect of treatment (24 h) of the THP-1 cells with the individual components A, B and C or the mixture A+B+C on production of IL-1β, in the presence of LPS. Ctrl: cells not treated and not stimulated (n=1; repetitions=2, plate read three times)

FIG. 12 shows the levels of IL-1β in cells treated with the various components and with the mixture following stimulation with the pro-inflammatory agent.

Table 16 presents the values of concentration of IL-1β (pg/ml).

Both in FIG. 12 and in Table 16, the values are given as mean±standard deviation of the concentrations derived from the values of absorbance of the samples (performed in duplicate and read in triplicate), interpolating them with the standard curve following the instructions supplied by the company.

TABLE 16

Values of IL-1β in THP-1 cells following treatment with the individual components A, B and C or the mixture A + B + C (n = 1; repetitions = 2, plate read three times).

| | Sample | | | | | |
|---|---|---|---|---|---|---|
| | Ctrl | Ctrl + LPS | A | B | C | A + B + C |
| IL-1β (pg/ml) | 3.71 ± 0.029 | 4.84 ± 0.032 | 4.05 ± 0.028 | 6.44 ± 0.029 | 4.98 ± 0.059 | 3.73 ± 0.394 |

Figure 13:
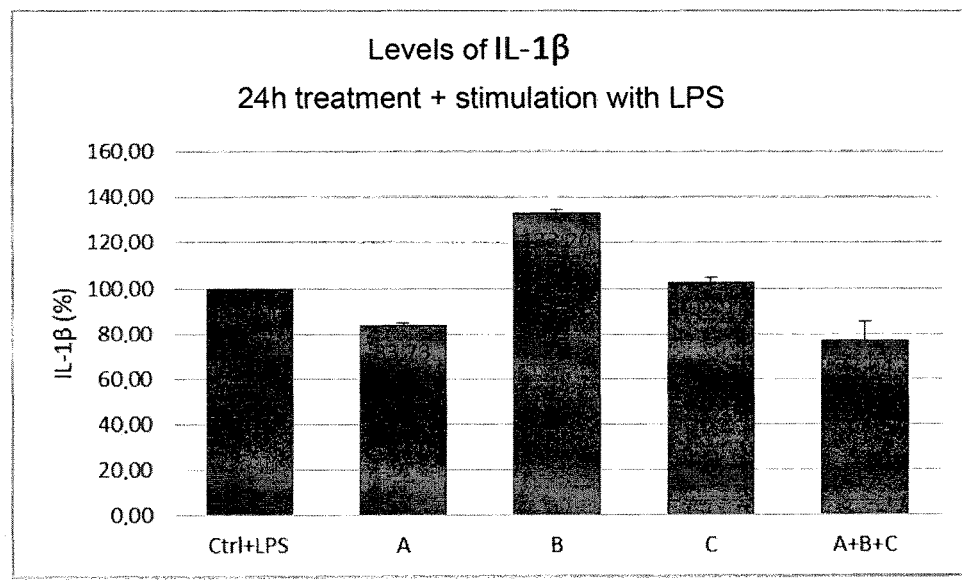
FIG. 13 is a graph showing the effect of treatment (24 hours) of the THP-1 cells with the individual components A, B and C or the mixture A+B+C on production of IL-1β, in the presence of LPS. Values expressed as a percentage relative to untreated cells (n=1; repetitions=2, plate read three times). * p≤0.05 ** p≤0.01: significance relative to the control (Kruskal-Wallis test)

FIG. 13 shows the levels expressed as a percentage, relative to stimulated untreated cells (Ctrl+LPS), after 24 hours of treatment with the three components and with the mixture A+B+C.

Table 17 presents these values together with their standard deviations.

TABLE 17

Values of IL-1β in THP-1 cells following treatment with the individual components A, B and C or the mixture A + B + C (n = 1; repetitions = 2, plate read three times).

| | Sample | | | | |
|---|---|---|---|---|---|
| | Ctrl + LPS | A | B | C | A + B + C |
| IL-1β (%) | 100 ± 0.032 | 83.73 ± 0.8 | 133.20 ± 1.17 | 102.91 ± 1.58 | 77.04 ± 8.22 |

The results obtained demonstrate that components B (lipoic acid, vitamin C and vitamin E acetate) and C (N-acetyl-L-carnitine) cause an increase in the levels of IL-1β after 24-hour treatment and stimulation with LPS.

Component A shows levels lower than the stimulated control. These data are in agreement with data in the literature: the anti-inflammatory activity of *curcuma* has in fact been demonstrated in the same cell line (Giri R. K., Rajagopal V., Kalra V. K., 2004 Curcumin, the active constituent of turmeric, inhibits amyloid peptide-induced cytochemokine gene expression and CCR5-mediated chemotaxis of THP-1 monocytes by modulating early growth response-1 transcription factor. J Neurochem.; 91: 1199-210).

The data relating to the anti-inflammatory activity of the three components combined (A+B+C) given in the graph indicate a decrease in the production of IL-1β after 24-hour treatment and then stimulation with LPS equal to 22.96%. This decrease was found to be statistically significant (Kruskal-Wallis test, ** p≤0.01) relative to the control even if not statistically significant relative to component A taken individually.

Evaluation of Expression of TNFα

The possible anti-inflammatory action of the individual components of Xinepa and the possible synergy were evaluated by measuring the levels of TNFα following stimulation with LPS. The negative control is represented by cells that were not treated and not stimulated; cells pre-treated (24 h) with the individual components or with the mixture were then incubated with LPS for 4 hours and the supernatant was collected for evaluating the interleukin levels.

Figure 14:
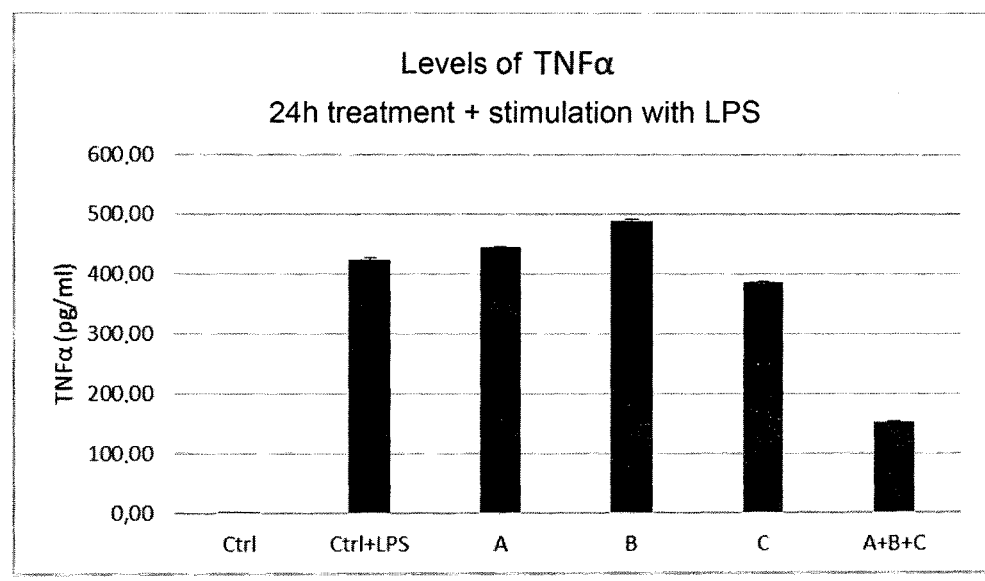
FIG. 14 is a graph showing the effect of treatment (24 hours) of the THP-1 cells with the individual components A, B and C or the mixture A+B+C on production of TNFα, in the presence of LPS. Ctrl: cells not treated and not stimulated (n=1; repetitions=2, plate read three times)

FIG. 14 shows the levels of TNFα in cells treated with the various components and with the mixture following stimulation with the pro-inflammatory agent.

Table 18 presents the values of concentration of TNFα (pg/ml).

Both in FIG. 14 and in Table 18, the values are reported as mean±standard deviation of the concentrations derived from the values of absorbance of the samples (performed in duplicate and read in triplicate), interpolating them with the standard curve following the instructions supplied by the company.

ing; as shown in the graph, the decrease in the production of TNFα after 24-hour treatment and then stimulation with LPS is equal to 67.74%. This decrease was found to be statistically significant (Kruskal-Wallis test, ** p≤0.01) and greater than that of component C taken individually, indicating a synergistic effect, of about three times, given by the three components combined.

Conclusions

The results obtained show that together, the three components of the supplement Xinepa cause a reduction in expression of the inflammatory cytokines analysed. This reduction was found to be statistically significant, greater than that produced by the individual components, the tumour necrosis factor being particularly evident. Thus, the anti-inflammatory synergy of the product Xinepa has been demonstrated. Specifically, the three components making up Xinepa are: *curcuma*, lipoic acid, vitamin C, vitamin E acetate and N-acetyl-L-carnitine. These were tested at non-cytotoxic concentrations, maintaining the proportions present in the dietary supplement. Analysis of expression of the cytokine TNFα following stimulation with LPS demonstrated the synergistic effect of the three components, with a reduction in the levels equal to about 68%, which was found to be statistically significant, and greater than three times. A similar result was obtained on analysing the cytokine IL-1β, confirming the synergistic effect of the components, although with a smaller reduction, equal to about 25%.

TABLE 18

Values of TNFα in THP-1 cells following treatment with the individual components A, B and C or the mixture A + B + C (n = 1; repetitions = 2, plate read three times).

| | Sample | | | | | |
|---|---|---|---|---|---|---|
| | Ctrl | Ctrl + LPS | A | B | C | A + B + C |
| TNFα (pg/ml) | 3.51 ± 0.11 | 424.12 ± 1.67 | 446.26 ± 1.73 | 488.10 ± 2.24 | 386.98 ± 1.24 | 153.78 ± 0.06 |

Figure 15:
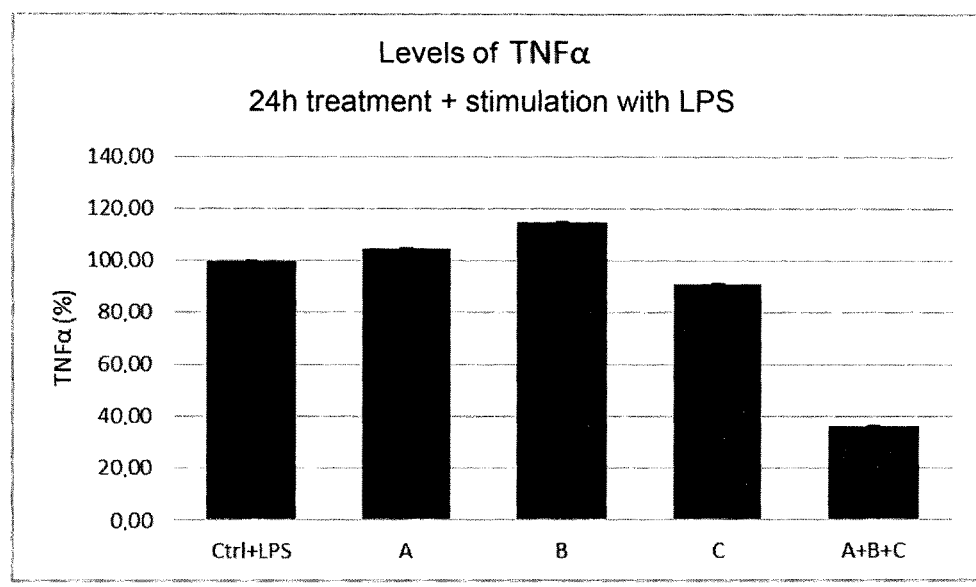
FIG. 15 is a graph showing the effect of treatment (24 hours) of the THP-1 cells with the individual components A, B and C or the mixture A+B+C on production of TNFα, in the presence of LPS. Values expressed as a percentage relative to untreated cells (n=1; repetitions=2, plate read three times). * p≤0.05 ** p≤0.01: significance relative to the control (Kruskal-Wallis test).

FIG. 15 shows the levels expressed as a percentage, relative to stimulated untreated cells (Ctrl+LPS), after 24 hours of treatment with the three components and with the mixture A+B+C.

Table 19 presents these values together with their standard deviations.

TABLE 19

Values of TNFα in THP-1 cells following treatment with the individual components A, B and C or the mixture A + B + C (n = 1; repetitions = 2, plate read three times).

| | Sample | | | | |
|---|---|---|---|---|---|
| | Ctrl + LPS | A | B | C | A + B + C |
| TNFα (%) | 100 ± 0.03 | 104.75 ± 0.01 | 115.09 ± 0.24 | 91.24 ± 0.22 | 36.26 ± 0.16 |

The results obtained demonstrate that components A (*curcuma*) and B (lipoic acid, vitamin C and vitamin E acetate) cause a slight increase in the levels of TNFα after 24-hour treatment and stimulation with LPS. Component C shows levels lower than the stimulated control.

The data relating to the anti-inflammatory activity of the three components combined (A+B+C) were very interest-

The invention claimed is:

1. A pharmaceutical composition or dietary supplement comprising a combination of *Curcuma longa* extract, acetyl ester of L-carnitine and alpha-lipoic acid, formulated for use in the treatment of neuropathies and/or neuropathic pain,
   wherein the pharmaceutical composition or dietary supplement is in a dosage form comprising about 400 mg of acetyl ester of L-carnitine, about 300 mg of alpha-lipoic acid and about 150 mg of *Curcuma longa* extract.

2. The pharmaceutical composition or dietary supplement according to claim 1, wherein said *Curcuma longa* extract has a curcumin titre of about 95%.

3. The pharmaceutical composition or dietary supplement according to claim 1, which is in an oral dosage form.

4. The pharmaceutical composition or dietary supplement according to claim 1, wherein the neuropathy is selected from the group consisting of peripheral neuropathy, inflammatory post-traumatic neuropathy, lumbosciatic syndrome, diabetic metabolic neuropathy, mechanical neuropathy due to nerve entrapment and compression, carpal tunnel syndrome, chemotherapy-induced neuropathy, antiretroviral therapy-induced neuropathy, zoster virus neuropathy, brachial nerve neuropathy due to vaccination.

5. The pharmaceutical composition or dietary supplement according to claim 1, further comprising one or more vitamins selected from the group consisting of vitamin C, vitamin E, vitamin B1, vitamin B2, vitamin B6 and vitamin B12.

6. The pharmaceutical according to claim 1, further comprising pharmaceutically acceptable excipients and/or binders and/or vehicles.

* * * * *